United States Patent
Shallom

(10) Patent No.: US 12,334,105 B2
(45) Date of Patent: Jun. 17, 2025

(54) DETECTING IMPAIRED PHYSIOLOGICAL FUNCTION BY SPEECH ANALYSIS

(71) Applicant: Cordio Medical Ltd., Or Yehuda (IL)

(72) Inventor: Ilan D. Shallom, Gedera (IL)

(73) Assignee: Cordio Medical Ltd., Or-Yehuda (IL)

( * ) Notice: Subject to any disclaimer, the term of this patent is extended or adjusted under 35 U.S.C. 154(b) by 729 days.

(21) Appl. No.: 17/531,828

(22) Filed: Nov. 22, 2021

(65) Prior Publication Data

US 2022/0165295 A1 May 26, 2022

Related U.S. Application Data

(60) Provisional application No. 63/116,949, filed on Nov. 23, 2020.

(51) Int. Cl.
| | |
|---|---|
| *G10L 25/66* | (2013.01) |
| *A61B 5/00* | (2006.01) |
| *A61B 5/08* | (2006.01) |
| *A61B 5/083* | (2006.01) |
| *A61B 5/087* | (2006.01) |
| *A61B 5/091* | (2006.01) |
| *G10L 25/15* | (2013.01) |
| *G10L 25/18* | (2013.01) |

(52) U.S. Cl.
CPC .............. *G10L 25/66* (2013.01); *A61B 5/082* (2013.01); *A61B 5/0836* (2013.01); *A61B 5/087* (2013.01); *A61B 5/091* (2013.01); *A61B 5/4803* (2013.01); *G10L 25/15* (2013.01); *G10L 25/18* (2013.01)

(58) Field of Classification Search
CPC .................................... A61B 5/08; A61B 5/09
See application file for complete search history.

(56) References Cited

U.S. PATENT DOCUMENTS

| | | | |
|---|---|---|---|
| 4,292,471 | A | 9/1981 | Kuhn et al. |
| 4,838,275 | A | 6/1989 | Lee |
| 5,853,005 | A | 12/1998 | Scanlon |
| 5,864,810 | A | 1/1999 | Digalakis et al. |
| 6,006,188 | A | 12/1999 | Bogdashevsky et al. |
| 6,168,568 | B1 | 1/2001 | Gavriely |
| 6,241,683 | B1 | 6/2001 | Macklem et al. |
| 6,289,313 | B1 | 9/2001 | Heinonen et al. |
| 6,389,393 | B1 | 5/2002 | Gong |

(Continued)

FOREIGN PATENT DOCUMENTS

| | | |
|---|---|---|
| CN | 102125427 A | 7/2011 |
| CN | 102423262 A | 4/2012 |

(Continued)

OTHER PUBLICATIONS

IN Application # 202147045344 Office Action dated Apr. 1, 2022.

(Continued)

*Primary Examiner* — Eric F Winakur
*Assistant Examiner* — Hy Khanh Doan
(74) *Attorney, Agent, or Firm* — Meitar Patents Ltd.; Daniel Kligler

(57) ABSTRACT

A method includes computing one or more values of at least one parameter at respective times during an exhalation of a subject, based on one or more properties of sound passing through air exhaled by the subject during the exhalation, the parameter being related to a concentration of a gas in the air. The method further includes generating an output in response to the values. Other embodiments are also described.

44 Claims, 6 Drawing Sheets

(56) References Cited

U.S. PATENT DOCUMENTS

| | | |
|---|---|---|
| 6,396,416 B1 | 5/2002 | Kuusela et al. |
| 6,527,729 B1 | 3/2003 | Turcott |
| 6,600,949 B1 | 7/2003 | Turcott |
| 7,092,874 B2 | 8/2006 | Clavbo |
| 7,225,013 B2 | 5/2007 | Geva et al. |
| 7,226,422 B2 | 6/2007 | Hatlestsad et al. |
| 7,267,652 B2 | 9/2007 | Coyle et al. |
| 7,283,962 B2 | 10/2007 | Meyerhoif et al. |
| 7,363,226 B2 | 4/2008 | Shiomi et al. |
| 7,398,213 B1 | 7/2008 | Levanon et al. |
| 7,457,753 B2 | 11/2008 | Moran et al. |
| 7,529,670 B1 | 5/2009 | Michaelis |
| 7,762,264 B1 | 7/2010 | Raming et al. |
| 8,478,596 B2 | 7/2013 | Schultz |
| 8,591,430 B2 | 11/2013 | Amurthur et al. |
| 8,684,900 B2 | 4/2014 | Tran |
| 8,689,606 B2 | 4/2014 | Schellekens et al. |
| 8,784,311 B2 | 7/2014 | Shrivastav et al. |
| 8,903,725 B2 | 12/2014 | Pilz |
| 9,070,357 B1 | 6/2015 | Kennedy et al. |
| 9,153,231 B1 | 6/2015 | Salvador et al. |
| 9,138,167 B1 | 9/2015 | Leydon |
| 9,445,763 B2 | 9/2016 | Davis et al. |
| 9,492,096 B2 | 11/2016 | Brockway et al. |
| 9,579,056 B2 | 2/2017 | Rosenbek et al. |
| 9,685,174 B2 | 6/2017 | Karam et al. |
| 9,922,641 B1 | 3/2018 | Chun |
| 10,311,980 B2 | 6/2019 | Kim et al. |
| 10,796,205 B2 | 10/2020 | Shi et al. |
| 10,896,765 B2 | 1/2021 | Kim et al. |
| 10,991,384 B2 | 4/2021 | Eyben et al. |
| 12,046,238 B2 | 7/2024 | Khaleghi |
| 2002/0059029 A1 | 5/2002 | Todder et al. |
| 2003/0115054 A1 | 6/2003 | Iso-Sipila et al. |
| 2003/0220790 A1 | 11/2003 | Kepuska |
| 2004/0097822 A1 | 5/2004 | Muz et al. |
| 2005/0038635 A1 | 2/2005 | Klefenz et al. |
| 2005/0060153 A1 | 3/2005 | Gable et al. |
| 2006/0058697 A1 | 3/2006 | Mochizuki et al. |
| 2006/0116878 A1 | 6/2006 | Nagamine |
| 2006/0167385 A1 | 7/2006 | Guion |
| 2006/0293609 A1 | 12/2006 | Stahmann et al. |
| 2007/0005357 A1 | 1/2007 | Moran et al. |
| 2007/0100623 A1 | 5/2007 | Hentschel et al. |
| 2007/0225975 A1 | 9/2007 | Imoto |
| 2007/0288183 A1 | 12/2007 | Bulkes et al. |
| 2008/0013747 A1 | 1/2008 | Tran |
| 2008/0275349 A1 | 11/2008 | Halperin et al. |
| 2009/0036777 A1 | 2/2009 | Zhang et al. |
| 2009/0043586 A1 | 2/2009 | MacAuslan |
| 2009/0099848 A1 | 4/2009 | Lerner et al. |
| 2009/0227888 A1 | 9/2009 | Salmi et al. |
| 2009/0326937 A1 | 12/2009 | Chitsaz et al. |
| 2010/0201807 A1 | 8/2010 | McPherson |
| 2011/0021940 A1 | 1/2011 | Chu et al. |
| 2011/0092779 A1 | 4/2011 | Chang et al. |
| 2011/0125044 A1 | 5/2011 | Rhee |
| 2011/0184250 A1 | 7/2011 | Schmidt et al. |
| 2012/0041279 A1 | 2/2012 | Freeman et al. |
| 2012/0116186 A1 | 5/2012 | Shrivastav et al. |
| 2012/0220899 A1 | 8/2012 | Oh et al. |
| 2012/0283598 A1 | 8/2012 | Horii et al. |
| 2012/0265024 A1 | 10/2012 | Shrivastav et al. |
| 2013/0018274 A1 | 1/2013 | O'Neill |
| 2013/0158434 A1 | 6/2013 | Shen et al. |
| 2013/0166279 A1 | 6/2013 | Dines et al. |
| 2013/0218582 A1 | 8/2013 | Lalonde |
| 2014/0005564 A1 | 1/2014 | Ivanovic et al. |
| 2014/0073993 A1 | 3/2014 | Poellabauer et al. |
| 2014/0153794 A1 | 6/2014 | Varaklis et al. |
| 2014/0249424 A1 | 9/2014 | Fan et al. |
| 2014/0294188 A1 | 10/2014 | Rini et al. |
| 2014/0302472 A1 | 10/2014 | Fletcher |
| 2014/0314212 A1 | 10/2014 | Bentley et al. |
| 2015/0073306 A1 | 3/2015 | Abeyratne et al. |
| 2015/0126888 A1 | 5/2015 | Patel et al. |
| 2015/0127350 A1 | 5/2015 | Agiomyrgiannakis |
| 2015/0216448 A1 | 8/2015 | Lotan et al. |
| 2015/0265205 A1 | 9/2015 | Rosenbek et al. |
| 2016/0015289 A1 | 1/2016 | Simon et al. |
| 2016/0045161 A1 | 2/2016 | Alshaer et al. |
| 2016/0081611 A1 | 3/2016 | Hampton et al. |
| 2016/0095545 A1 | 4/2016 | Levanon |
| 2016/0113618 A1 | 4/2016 | Su et al. |
| 2016/0249842 A1 | 9/2016 | Ohana Lubelchick |
| 2016/0302003 A1 | 10/2016 | Rahman et al. |
| 2017/0069312 A1 | 3/2017 | Sundararajan et al. |
| 2017/0084295 A1 | 3/2017 | Tsiartas et al. |
| 2017/0262606 A1 | 9/2017 | Abdullah et al. |
| 2017/0280239 A1 | 9/2017 | Sekiya et al. |
| 2017/0325779 A1 | 11/2017 | Spina et al. |
| 2017/0354363 A1 | 12/2017 | Quatieri et al. |
| 2018/0004913 A1 | 1/2018 | Ghasemzadeh et al. |
| 2018/0108440 A1 | 4/2018 | Stevens et al. |
| 2018/0125444 A1 | 5/2018 | Kahlman et al. |
| 2018/0214061 A1 | 8/2018 | Knoth et al. |
| 2018/0296092 A1 | 10/2018 | Hassan et al. |
| 2019/0080803 A1 | 3/2019 | Lotan et al. |
| 2019/0130910 A1 | 5/2019 | Kariya et al. |
| 2019/0221317 A1 | 7/2019 | Kempanna et al. |
| 2019/0311815 A1 | 10/2019 | Kim et al. |
| 2019/0385711 A1 | 12/2019 | Shriberg et al. |
| 2020/0098384 A1 | 3/2020 | Nematihosseinabadi et al. |
| 2020/0118583 A1 | 4/2020 | Shallom et al. |
| 2020/0152226 A1 | 5/2020 | Anushiravani et al. |
| 2020/0168230 A1 | 5/2020 | Roh et al. |
| 2020/0294527 A1 | 9/2020 | Shallom et al. |
| 2020/0294531 A1 | 9/2020 | Shallom et al. |
| 2021/0065676 A1 | 3/2021 | Abrami et al. |
| 2021/0110894 A1 | 4/2021 | Shriberg et al. |
| 2021/0193169 A1 | 6/2021 | Faizakof et al. |
| 2021/0275037 A1 | 9/2021 | Shallom |
| 2021/0407519 A1 | 9/2021 | Shallom et al. |
| 2022/0130415 A1 | 4/2022 | Garrison et al. |
| 2022/0328064 A1 | 10/2022 | Shriberg et al. |
| 2022/0415308 A1 | 12/2022 | Berisha et al. |
| 2023/0072242 A1 | 3/2023 | Kim et al. |
| 2023/0190177 A1 | 6/2023 | Shor et al. |
| 2023/0352013 A1 | 11/2023 | Khaleghi |

FOREIGN PATENT DOCUMENTS

| | | |
|---|---|---|
| CN | 202261466 U | 5/2012 |
| CN | 102497472 A | 6/2012 |
| CN | 107622797 A | 1/2018 |
| DE | 102015218948 A1 | 3/2017 |
| EP | 1855594 A1 | 11/2007 |
| EP | 2124223 A1 | 11/2009 |
| EP | 2438863 A1 | 4/2012 |
| FR | 2672793 A1 | 8/1992 |
| GB | 1219618 A | 1/1971 |
| GB | 2493458 A | 2/2013 |
| JP | 04082538 A | 3/1992 |
| JP | 09173320 A | 7/1997 |
| JP | 2003044078 A | 2/2003 |
| JP | 2004302786 A | 10/2004 |
| JP | 2006230548 A | 9/2006 |
| JP | 2016006504 A | 1/2016 |
| JP | 2017191166 A | 10/2017 |
| JP | 6263308 B1 | 1/2018 |
| SE | 508439 C2 | 10/1998 |
| WO | 03068062 A1 | 8/2003 |
| WO | 2005074799 A1 | 8/2005 |
| WO | 2006033044 A3 | 3/2006 |
| WO | 2006079062 A1 | 7/2006 |
| WO | 2010004025 A1 | 1/2010 |
| WO | 2010015865 A1 | 2/2010 |
| WO | 2010123483 A2 | 10/2010 |
| WO | 2012038903 A2 | 3/2012 |
| WO | 2012104743 A2 | 8/2012 |
| WO | 2013043847 A1 | 3/2013 |
| WO | 2013170131 A1 | 11/2013 |
| WO | 2014037843 A1 | 3/2014 |
| WO | 2014045257 A1 | 3/2014 |

(56) References Cited

FOREIGN PATENT DOCUMENTS

| | | |
|---|---|---|
| WO | 2014188408 A1 | 11/2014 |
| WO | 2016028495 A1 | 2/2016 |
| WO | 2017060828 A1 | 4/2017 |
| WO | 2017068582 A1 | 7/2017 |
| WO | 2017147221 A1 | 8/2017 |
| WO | 2018021920 A1 | 2/2018 |
| WO | 2019089830 A1 | 5/2019 |
| WO | 2019210261 A1 | 10/2019 |

OTHER PUBLICATIONS

Gupta et al., "Characterizing Exhaled Airflow from Breathing and Talking," Indoor Air, vol. 20, pp. 31-39, year 2010.

U.S. Appl. No. 17/074,653 Office Action dated Mar. 9, 2022.

Bhagya et al., "Speed of Sound-Based Capnographic Sensor with Second-Generation CNN for Automated Classification of Cardiorespiratory Abnormalities," IEEE Sensors Journal, vol. 19, issue 19, pp. 8887-8894, Oct. 1, 2019.

Mirza et al., "Analytical Modeling and Simulation of a CMOS-MEMS Cantilever Based CO2 Sensor for Medical Applications," Proceedings IEEE Regional Symposium on Micro and Nanoelectronics, pp. 70-73, Sep. 27, 2013.

International Application # PCT/IB2021/060800 Search Report dated Mar. 21, 2022.

IN Application # 202147045402 Office Action dated Mar. 14, 2022.

EP Application # 21209891.7 Search Report dated Apr. 13, 2022.

International Application # PCT/IB2024/054360 Search Report dated Jun. 28, 2024.

JP Application # 2022576351 Office Action dated Jul. 2, 2024.

U.S. Appl. No. 17/902,836 Office Action Jul. 8, 2024.

International Application # PCT/IB2024/054359 Search Report dated Jul. 9, 2024.

AU Application # 2021384028 Office Action Aug. 15, 2024.

EP Application # 24181539.8 Search Report dated Sep. 4, 2024.

AU Application # 2020235966 Office Action dated Jun. 30, 2022.

AU Appliation # 2020234072 Office Action dated Aug. 25, 2022.

U.S. Appl. No. 17/074,653 Office Action dated Sep. 2, 2022.

Larson et al., "SpiroSmart: using a microphone to measure lung function on a mobile phone", Proceedings of the 2012 ACM Conference on Ubiquitous Computing (UbiComp '12), pp. 280-289, Sep. 5-8, 2012.

Abushakra et al., "An Automated Approach Towards Estimating Lung Capacity from Respiration Sounds", IEEE Healthcare Innovations Conference (HIC'12), pp. 1-5, Jan. 2012.

Williammson et al., "Vocal and Facial Biomarkers of Depression Based on Motor Incoordination and Timing", 4th International Audio/Visual Emotion Challenge and Workshop: Depression Challenge, Orlando, Florida, USA , pp. 1-8, Nov. 7, 2014.

Ciccarelli et al., "Neurophysiological Vocal Source Modeling for Biomarkers of Disease", Interspeech 2016: Understanding Speech Processing in Humans and Machines, Technical Program, San Francisco, USA, pp. 1-7, Sep. 8-12, 2016.

Helfer et al., "Classification of depression state based on articulatory precision", Proceedings of the 14th Annual Conference of the International Speech Communication Association (Interspeech), pp. 2172-2176, year 2013.

Horwitz., "Vocal Modulation Features in the Prediction of Major Depressive Disorder Severity", pp. 1-115, Master Thesis, Massachusetts Institute of Technology, Sep. 2014.

Hillel., "Using phonation time to estimate vital capacity in amyotrophic lateral sclerosis", Arch Phys Med Rehabil, vol. 70, pp. 618-620, Aug. 1989.

Yanagihara., "Phonation and Respiration", Folia Phoniat, vol. 18, pp. 323-340, 1966.

Dewar et al., "Chronic obstructive pulmonary disease: diagnostic considerations.", American Academy of Family Physicians, vol. 73, pp. 669-676, Feb. 2006.

Solomon et al., "Respiratory and laryngeal contributions to maximum phonation duration", Journal of voice, vol. 14, No. 3, pp. 331-340, Sep. 2000.

Dogan et al., "Subjective and objective evaluation of voice quality in patients with asthma", Journal of voice, vol. 21, No. 2, pp. 224-230, Mar. 2007.

Orenstein et al., "Measuring ease of breathing in young patients with cystic fibrosis", Pediatric Pulmonology, vol. 34, No. 6, pp. 473-477, Aug. 8, 2002.

Lee et al., "Speech Segment Durations Produced by Healthy and Asthmatic Subjects", Journal of Speech and Hearing Disorders, vol. 653, pp. 186-193, May 31, 1988.

Hickey, "App lets you monitor lung health using only a smartphone", pp. 1-5, Sep. 18, 2012.

Gandler et al., "Mobile FEV: Evaluation of iPhone Spirometer", pp. 1-1, Feb. 14, 2013.

Abushakra et al., "Lung capacity estimation through acoustic signal of breath", 13th IEEE International Conference on BioInformatics and BioEngineering, pp. 386-391, Nov. 11-13, 2012.

G.P. Imports, Inc., "Spirometer Pro", pp. 1-3, Jan. 8, 2010.

Murton et al., "Acoustic speech analysis of patients with decompensated heart failure: A pilot study", The Journal of the Acoustical Society of America, vol. 142, Issue 4, pp. 1-28, Oct. 24, 2017.

Gillespie et al., "The Effects of Hyper- and Hypocapnia on Phonatory Laryngeal Airway Resistance in Women", Research Article, Journal of Speech, Language, and 638 Hearing Research , vol. 58 , pp. 638-652, Jun. 2015.

Wang et al., "Accuracy of perceptual and acoustic methods for the detection of inspiratory loci in spontaneous speech", Behavior Research Methods, vol. 44, Issue 4, pp. 1121-1128, Dec. 2012.

Mulligan et al., "Detecting regional lung properties using audio transfer functions of the respiratory system", 31st Annual International Conference of the IEEE EMBS, pp. 5697-5700, Sep. 2-6, 2009.

Walia et al., "Level of Asthma: A Numerical Approach based on Voice Profiling", IJEDR(International Journal of Engineering Development and Research), vol. 4, Issue 4, pp. 717-722, 2016.

Sakoe et al., "Dynamic Programming Algorithm Optimization for Spoken Word Recognition", IEEE Transactions on Acoustics, Speech and Signal Processing, vol. ASSP-26, No. 1, pp. 43-49, Feb. 1978.

Rabiner, L., "A tutorial on hidden Markov models and selected applications in speech recognition," Proceedings of the IEEE, vol. 77, issue 2 , pp. 257-286, Feb. 1989.

Rabiner et al., "Fundamentals of Speech Recognition", Prentice Hall, pp. 1-18 (related section 6.4.3.), year 1993.

Lee et al., Consistency of acoustic and aerodynamic measures of voice production over 28 days under various testing conditions, Journal of Voice, Elsevier Science , US, vol. 13, Issue 4, pp. 477-483, Dec. 1, 1999.

AU Application # 2021384028 Office Action dated Feb. 29, 2024.

Christina et al., "HMM-based speech recognition system for the dysarthric speech evaluation of articulatory subsystem", International Conference on Recent Trends in Information Technology, pp. 54-59, Apr. 1, 2012.

Wang et al., "Vocal folds disorder detection using pattern recognition methods", 29th Annual International Conference of the IEEE Engineering in Medicine and Biology Society, pp. 3253-3256, Aug. 22-26, 2007.

Masada et al., "Feature Extraction by ICA and Clustering for Lung Sound Classification", IPSJ Symposium Series, vol. 2007, pp. 1-9, year 2007.

Ramirez et al.,"Voice activity detection. Fundamentals and speech recognition system robustness", Robust Speech Recognition and Understanding, I-Tech, Vienna, Austria, pp. 1-24, Jun. 2007.

Bachu et al., "Separation of Voiced and Unvoiced Speech Signals using Energy and Zero Crossing Rate", ASEE Regional Conference, pp. 1-7, year 2008.

Ney, "The Use of a One-Stage Dynamic Programming Algorithm for Connected Word Recognition," IEEE Transactions on Acoustics, Speech, and Signal Processing, vol. ASSP-32, No. 2, pp. 263-271, Apr. 1984.

(56) References Cited

OTHER PUBLICATIONS

Rao et al., "Acoustic Methods for Pulmonary Diagnosis," HHS Public Access, Author manuscript, pp. 1-39, year 2020 (final version published in IEEE Reviews in Biomedical Engineering, vol. 12, pp. 221-239, year 2019).
Cohen, "Signal processing methods for upper airway and pulmonary dysfunction diagnosis," IEEE Engineering in Medicine and Biology Magazine, vol. 9, No. 1, pp. 72-75, Mar. 1, 1990.
Wikipedia, "Breathing," pp. 1-13, last edited Oct. 17, 2021, as downloaded from https://en.wikipedia.org/wiki/Breathing.
"Sound Speed in Gases," Sound and Hearing, HyperPhysics, Department of Physics and Astronomy, Georgia State University, USA, pp. 1-3, year 2017, as downloaded from http://hyperphysics.phy-astr.gsu.edu/hbase/Sound/souspe3.html.
"Echo Devices," Amazon.com, Inc, Interest-Based Ads, pp. 1-6, year 2021, as downloaded from https://www.amazon.com/echo-devices/s?k=echo+devices.
"The Best Google Home Speakers in 2021," Tom's Guide, Future US Inc., pp. 1-21, year 2021, as downloaded from https://www.tomsguide.com/best-picks/best-google-home-speakers.
West et al., "Measurements of Pulmonary Gas Exchange Efficiency using Expired Gas and Oximetry: Results in Normal Subjects," American Journal of Physiology—Lung Cellular and Molecular Physiology, vol. 314, No. 4, pp. L686-L689, year 2018.
West et al., "A New Method for Noninvasive Measurement of Pulmonary Gas Exchange Using Expired Gas," Respiratory Physiology & Neurobiology, vol. 247, pp. 112-115, year 2018.
Huang et al., "An Accurate Air Temperature Measurement System Based on an Envelope Pulsed Ultrasonic Time-of-Flight Technique," Review of Scientific Instruments, vol. 78, pp. 115102-1-115102-9, year 2007.
Jedrusyna, "An Ultrasonic Air Temperature Meter," Recent Advances in Mechatronics, Springer, Berlin, Heidelberg, pp. 85-89, year 2010.
Cramer, "The Variation of the Specific Heat Ratio and the Speed of Sound in Air with Temperature, Pressure, Humidity, and CO2 Concentration," Journal of the Acoustical Society of America, vol. 93, No. 5, pp. 2510-2516, May 1993.
U.S. Appl. No. 16/807,178 Office Action dated Feb. 24, 2022.
International Application # PCT/IB2021/054952 Search Report dated Jan. 30, 2022.
U.S. Appl. No. 16/914,524 Office Action dated Jan. 26, 2022.
AU Application # 2019356224 Office Action dated Jan. 17, 2022.
EP Application # 20158058.6 Summons to Oral Proceedings dated Apr. 19, 2023.
EP Application # 19201720.0 Office Action dated Mar. 30, 2023.
EP Application # 21209891.7 Office Action dated May 19, 2023.
JP Application # 2021-517971 Office Action dated May 16, 2023.
Indian Application # 202247066856 Office Action dated Mar. 29, 2023.
Sakran et al., "A Review: Automatic Speech Segmentation", International Journal of Computer Science and Mobile Computing (IJCSMC), vol. 6, issue 4, pp. 308-315, Apr. 2017.
Nicora et al., "Evaluating pointwise reliability of machine learning prediction", Journal of Biomedical Informatics, vol. 127, pp. 1-15, Mar. 2022.
Haimi-Cohen et al., U.S. Appl. No. 18/328,739, filed Jun. 4, 2023.
Haimi-Cohen et al., U.S. Appl. No. 18/328,738, filed Jun. 4, 2023.
Katsir et al., U.S. Appl. No. 18/319,518, filed May 18, 2023.
Haimi-Cohen et al., U.S. Appl. No. 18/105,848, filed Feb. 5, 2023.
Haimi-Cohen et al., U.S. Appl. No. 18/105,847, filed Feb. 5, 2023.
U.S. Appl. No. 17/233,487 Office Action dated Dec. 29, 2022.
EP Application # 21209891.7 Office Action dated Sep. 28, 2023.
CN Application # 2020800180012 Office Action dated Jan. 30, 2024.
IN Application # 202347030550 Office Action dated Dec. 13, 2023.
CN Application # 2019800670875 Office Action dated Dec. 20, 2023.
JP Application # 2021549583 Office Action dated Dec. 25, 2023.
JP Application # 2021551893 Office Action dated Dec. 25, 2023.
CN Application # 202080017839X Office Action dated Jan. 27, 2024.
International Application # PCT/IB2024/050483 Search Report dated May 7, 2024.
EP Application # 21832054.7 Search Report dated Mar. 11, 2024.
JP Application # 2022548568 Office Action dated Oct. 29, 2024.
U.S. Appl. No. 18/105,848 Office Action dated Jan. 21, 2025.
CN Application # 202180045274.0 Office Action dated Feb. 28, 2025.
U.S. Appl. No. 18/328,738 Office Action dated Apr. 11, 2025.
U.S. Appl. No. 18/328,739 Office Action dated Apr. 25, 2025.
U.S. Appl. No. 18/105,847 Office Action dated May 6, 2025.
CN Application # 202180017631.2 Office Action dated Mar. 31, 2025.
Voleti et al., "A Review of Automated Speech and Language Features for Assessment of Cognitive and Thought Disorders," IEEE Journal of Selected Topics in Signal Processing, vol. 14, No. 2, pp. 282-298, Feb. 2020.

DETECTING IMPAIRED PHYSIOLOGICAL FUNCTION BY SPEECH ANALYSIS

CROSS-REFERENCE TO RELATED APPLICATIONS

The present application claims the benefit of U.S. Provisional Application 63/116,949, entitled "Detecting impaired physiological function by speech analysis," filed Nov. 23, 2020, whose disclosure is incorporated herein by reference.

FIELD OF THE INVENTION

The present invention is related to the diagnosis and treatment of physiological disorders.

BACKGROUND

During exhalation, carbon dioxide ($CO_2$) diffuses from the pulmonary capillaries into the lungs, while oxygen ($O_2$) diffuses from the lungs into the pulmonary capillaries. For each of these gases, equilibrium is reached (i.e., the exchange of the gas stops) when the partial pressure of the gas in the lungs equals the partial pressure of the gas in the pulmonary capillaries. In general, equilibrium for $CO_2$ is reached prior to equilibrium for $O_2$.

The main components in exhaled air are nitrogen ($N_2$), $O_i$ water ($H_2O$), and $CO_2$. Hence, the molecular mass $MA(t)$ of exhaled air, as a function of a time variable t, is approximately equal to $C_{N_2}(t)*M_{N_2}+C_{O_2}(t)*M_{O_2}+C_{H_2O}(t)*M_{H_2O}+C_{CO_2}(t)C*M_{CO_2}$, where $C_x(t)$ is the time-varying concentration of any component x in the exhaled air and $M_x$ is the molecular mass of the component. In general, $M_I=M_A(0)$, the initial molecular mass of the air in the lungs before any gas exchange takes place, depends only on environmental conditions.

At any time during an exhalation, in approximation:

$$M_A(t)=(1-C'_{O_2}(t)-C'_{CO_2}(t))*M_I+C'_{O_2}(t)*M_{O_2}+C'_{CO_2}(t)*M_{CO_2} \quad (1)$$

where $-C'_{O_2}(t)$ is the concentration of $O_2$ that diffused from the lungs (i.e., the volume of $O_2$ that diffused from the lungs divided by the volume of air in the lungs) before time t, and $C'_{CO_2}(t)$ is the concentration of $CO_2$ that diffused into the lungs before time t. When equilibrium for oxygen is reached at time $t_E$, $C'_{CO_2}(t_E)=-C'_{O_2}(t_E)$, such that:

$$M_E=M_A(t_E)=M_I+C'C_{CO_2,E}*(M_{CO_2}-M_{O_2}) \approx M_I + 12*C'_{CO_2,E} \quad (2).$$

(The approximation $M_{CO_2}-M_{O_2} \approx 12$, which is assumed for the remainder of the present description, follows from $M_{O_2} \approx 32$ g/mol and $M_{CO_2} \approx 44$ g/mol.)

In general, two physical mechanisms govern the changes in the concentrations of $CO_2$ and $O_2$ during exhalation: diffusion and perfusion. Diffusion causes the gases to move across the alveolar walls, from the side of higher concentration to the side of lower concentration. The rate of diffusion is proportional to the concentration gradient across the alveolar walls and to a diffusion constant. Perfusion refers to the flow of blood through the alveolar capillaries.

In some subjects, the flow of blood through the alveolar capillaries is sufficiently fast so as not to inhibit the rate of diffusion. In other words, the rate of change of the concentration of each of the gases is diffusion-constrained. In general, for diffusion-constrained gas exchange, $C'_{O_2} \approx 0$ when $CO_2$ reaches equilibrium at time $t_{E0}<t_E$. Hence, from equation (1):

$$M_C=M_A(t_{E0}) \approx (1-C'_{CO_2,E})*M_I+C'_{CO_2,E}*M_{CO_2} \quad (3)$$

Given two molecular masses $M_A(t_1)$ and $M_A(t_2)$ where $t_1<t_2 \leq t_{E0}$, it follows, from equation (1), that:

$$C'_{CO_2}(t_2)-C'_{CO_2}(t_1)=(M_A(t_2)-M_A(t_1))/(M_{CO_2}-M_I) \quad (4).$$

For $t_2>t_1 \geq t_{E0}$, it follows, from equation (1), that:

$$C'_{O_2}(t_2)-C'_{O_2}(t_1)=(M_A(t_2)-M_A(t_1))/(M_{O_2}-M_I) \quad (5).$$

From the above, it may be deduced that, for diffusion-constrained gas exchange, $M_A(t)$ changes in two stages. In the first stage, $M_A(t)$ increases until reaching a maximum of MC at $t=t_{E0}$. In the second stage, $M_A(t)$ drops exponentially to ME, which is typically closer to $M_C$ than to $M_I$. The rate at which $M_A(t)$ changes in each stage depends on the rate of diffusion, which may be impaired in some subjects.

In other subjects, on the other hand, the blood flow rate through the alveolar capillaries limits the rate of diffusion; in other words, the rate of concentration change is perfusion-constrained. For such subjects, the rate of concentration change is capped by a maximum value, which is a function of the rate of blood flow.

In particular, for perfusion-constrained gas exchange, $C'_{CO_2}(t) \approx -C'_{O_2}(t)$ at all times, and so, from equation (1):

$$C'_{CO_2}(t_2)-C'_{CO_2}(t_1)=C'_{O_2}(t_1)-C'_{O_2}(t_2)=(M(t_2)-M(t_1))/12 \quad (6).$$

Thus, perfusion-constrained gas exchange takes place in a single stage, in which $M_A(t)$ increases linearly until reaching $M_E$.

In yet other subjects, the exchange of $O_2$ is diffusion-constrained, but the exchange of $CO_2$ is perfusion-constrained. In this case, there are two stages, as in the case of complete diffusion constraint. However, the first stage is relatively long, and $M_C$ is relatively close to $M_E$.

The speed "v" of sound in a gas is a function of the molecular mass "M" of the gas. (In this context, the term "gas" includes, within its scope, a mixture of gases such as $CO_2$, $O_2$, $N_2$, and water vapor.) For example, for an ideal gas, $$v = \sqrt{\gamma RT/M}, \quad (7)$$

where $\gamma$ is the adiabatic constant of the gas, R is the universal gas constant, and T is the temperature of the gas in Kelvins.

U.S. Pat. No. 8,689,606 describes a sensor chip for gas having cells for emitting and receiving ultrasound and being configured for a sufficiently large frequency range and for measuring concentration of at least one of the gas components based on at least two responses within the range. The frequency range can be achieved by varying the size of cell membranes, varying bias voltages, and/or varying air pressure for an array of cMUTs or MEMS microphones. The sensor chip can be applied in, for example, capnography. A measurement air chamber is implemented in the respiratory pathway, and it and/or the pathway may be designed to reduce turbulence in the exhaled breath subject to ultrasound interrogation. The chip can be implemented as self-contained in the monitoring of parameters, obviating the need for off-chip sensors.

US Patent Application Publication 2019/0080803 describes an apparatus including a network interface and a processor. The processor is configured to receive, via the network interface, speech of a subject who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition.

West, John B., et al., "Measurements of pulmonary gas exchange efficiency using expired gas and oximetry: results in normal subjects," American Journal of Physiology-Lung Cellular and Molecular Physiology 314.4 (2018): L686-L689 describes a noninvasive method for measuring the efficiency of pulmonary gas exchange in patients with lung disease. The patient wears an oximeter, and the partial pressures of oxygen and carbon dioxide in inspired and expired gas is measured using miniature analyzers.

West, John B., and G. Kim Prisk. "A new method for noninvasive measurement of pulmonary gas exchange using expired gas," Respiratory physiology & neurobiology 247 (2018): 112-115 describes how the composition of expired gas can be used in conjunction with pulse oximetry to obtain useful measures of gas exchange efficiency.

SUMMARY OF THE INVENTION

There is provided, in accordance with some embodiments of the present invention, a system including an output device and one or more processors. The processors are configured to cooperatively carry out a process that includes computing one or more values of at least one parameter at respective times during an exhalation of a subject, based on one or more properties of sound passing through air exhaled by the subject during the exhalation, the parameter being related to a concentration of a gas in the air, and generating an output, via the output device, in response to the values.

In some embodiments, the system further includes a sensor configured to measure a speed of the sound, and the process includes computing the values based on the speed.

In some embodiments, the system further includes a sensor configured to measure a baseline concentration of the gas in other exhaled air, and the process includes computing the values based on the baseline concentration.

There is further provided, in accordance with some embodiments of the present invention, a method including computing one or more values of at least one parameter at respective times during an exhalation of a subject, based on one or more properties of sound passing through air exhaled by the subject during the exhalation, the parameter being related to a concentration of a gas in the air, and generating an output in response to the values.

In some embodiments, the output indicates a state of the subject with respect to a physiological condition selected from the group of conditions consisting of: heart failure, asthma, hypobaropathy, hypercapnia, Chronic Obstructive Pulmonary Disease (COPD), and Interstitial Lung Disease (ILD).

In some embodiments, the method further includes, based on the values, identifying an extent to which a rate of change in the concentration is perfusion-constrained, and the output indicates the extent to which the rate of change is perfusion-constrained.

In some embodiments,
computing the one or more values of the at least one parameter includes computing multiple values of the concentration,
the method further includes, based on the multiple values of the concentration, computing a rate of change of the concentration, and
generating the output includes generating the output in response to the rate of change.

In some embodiments, generating the output includes generating the output in response to comparing the rate of change to a baseline rate of change.

In some embodiments,
computing the one or more values of the at least one parameter further includes computing multiple molecular-mass values of a molecular mass of the air,
the method further includes identifying an extent to which the rate of change is perfusion-constrained, and
computing the rate of change includes computing the rate of change based on the molecular-mass values and in response to identifying the extent to which the rate of change is perfusion-constrained.

In some embodiments, computing the rate of change includes computing the rate of change as a function of:
another rate of change of the molecular mass, and
at least one constant that depends on the extent to which the rate of change is perfusion-constrained.

In some embodiments, the one or more values include an equilibrium value of the parameter.

In some embodiments, the equilibrium value includes a $CO_2$-equilibrium value of a $CO_2$-concentration of $CO_2$ in the air.

In some embodiments, computing the $CO_2$-equilibrium value includes computing the $CO_2$-equilibrium value based on a baseline $CO_2$-equilibrium value that was measured prior to the exhalation.

In some embodiments, the sound is emitted by the subject while producing the exhalation.

In some embodiments, the sound belongs to speech of the subject, and computing the values includes computing the values based on a speech signal representing the speech.

In some embodiments, computing the values includes:
selecting portions of the speech signal recorded at the times, respectively;
computing respective spectral envelopes of the portions; and
computing the values based on respective expansions or contractions of the spectral envelopes relative to respective corresponding baseline spectral envelopes.

In some embodiments, the values include respective expansion factors that quantify the expansions or contractions.

In some embodiments, the baseline spectral envelopes belong to respective baseline signal-portions corresponding to the portions of the signal, respectively.

In some embodiments, the baseline signal-portions are other portions of the speech signal.

In some embodiments, the baseline signal-portions belong to a reference speech signal.

In some embodiments, the reference speech signal represents other speech uttered while in a known physiological state, and the output indicates a physiological state of the subject relative to the known physiological state.

In some embodiments, the reference speech signal represents other speech, and computing the values includes computing the values based on one or more measured properties of other air exhaled during the other speech.

In some embodiments, the reference speech signal represents other speech uttered by the subject.

In some embodiments, computing the values includes computing the values while identifying the correspondence between the baseline signal-portions and the portions of the speech signal, by varying the correspondence and expanding or contracting the spectral envelopes or the baseline spectral envelopes so as to minimize a sum of respective distance measures for the portions, the distance measure for each of the portions being a distance between (i) spectral coefficients of the portion and (ii) baseline spectral coefficients of the baseline signal-portion to which the portion corresponds, following the expansion or contraction.

In some embodiments, computing the values includes computing the values under a constraint that the values vary in accordance with a predefined function.

In some embodiments, the method further includes, prior to computing the values, identifying the correspondence between the portions and the baseline signal-portions by minimizing a sum of respective distance measures for the portions, the distance measure for each of the portions being a distance between (i) spectral coefficients of the portion and (ii) baseline spectral coefficients of the baseline signal-portion to which the portion corresponds.

In some embodiments, computing the values includes computing the values based on, for each of the portions, a statistic of respective ratios between (i) one or more formant frequencies of the portion, and (ii) corresponding formant frequencies in the baseline spectrum for the portion.

In some embodiments, the values include respective expansion factors that quantify the expansions or contractions, and the expansion factor for each portion minimizes a distance between (i) spectral coefficients of the portion and (ii) baseline spectral coefficients of the baseline spectrum for the portion, following an application of the expansion factor to the spectral coefficients or to the baseline spectral coefficients.

In some embodiments, computing the values includes computing the values based on respective measured speeds of the sound.

There is further provided, in accordance with some embodiments of the present invention, a computer software product including a tangible non-transitory computer-readable medium in which program instructions are stored. The instructions, when read by one or more processors, cause the processors to cooperatively carry out a process that includes computing one or more values of at least one parameter at respective times during an exhalation of a subject, based on one or more properties of sound passing through air exhaled by the subject during the exhalation, the parameter being related to a concentration of a gas in the air, and generating an output in response to the values.

The present invention will be more fully understood from the following detailed description of embodiments thereof, taken together with the drawings, in which:

DETAILED DESCRIPTION OF EMBODIMENTS

Overview

Figure 1:
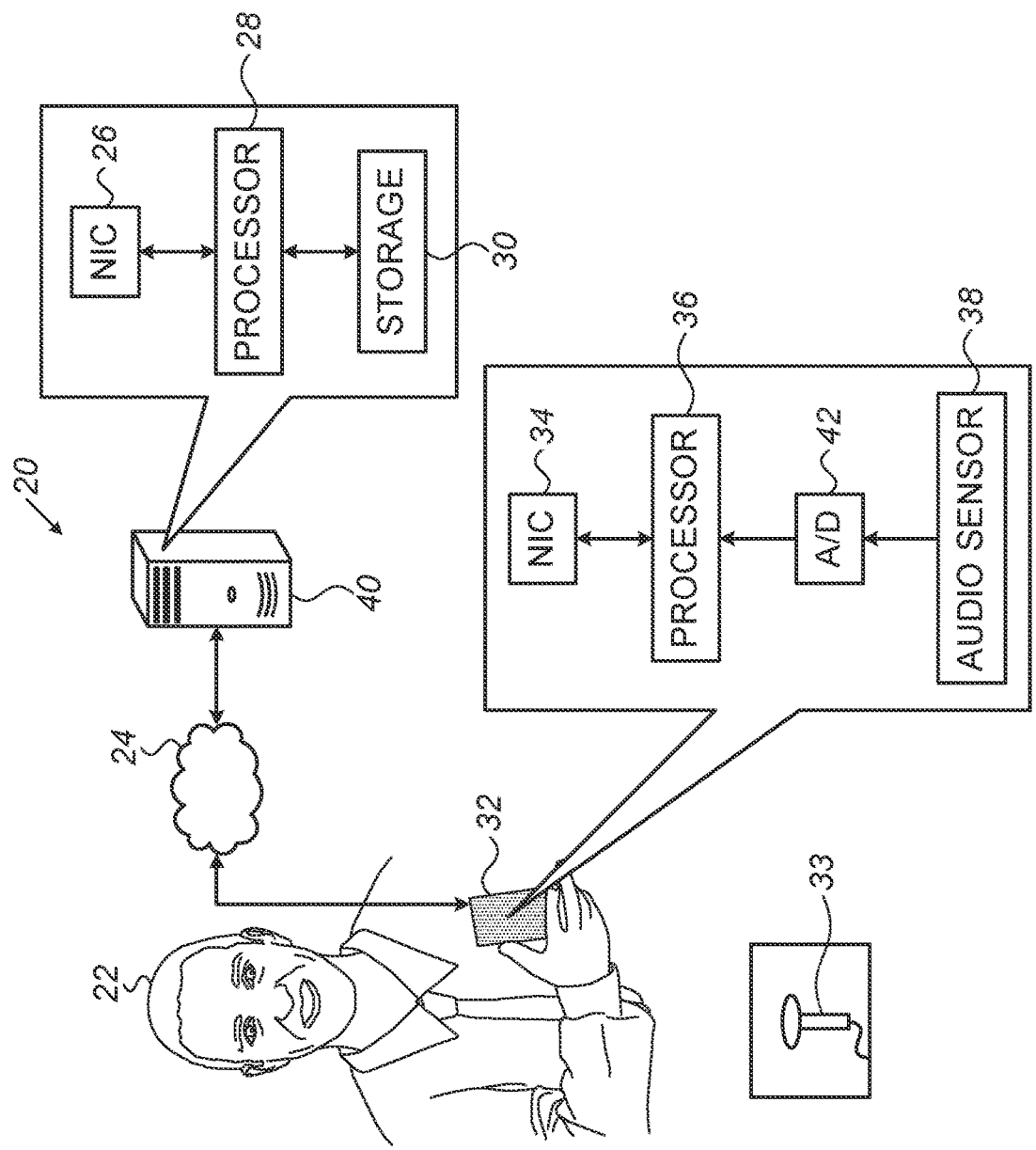
FIG. 1 is a schematic illustration of a system for evaluating the physiological state of a subject, in accordance with some embodiments of the present invention.

Many conventional techniques for assessing impaired cardiovascular or pulmonary function in a subject require the subject to visit a hospital or clinic, and/or require the use of a specialized device. Testing for such physiological problems may thus be inconvenient and/or expensive.

Embodiments of the present invention therefore provide improved techniques for diagnosing such physiological problems. These techniques capitalize on the fact that the physiological state of a subject may affect the concentrations of gases in the air exhaled by the subject, and hence, the properties of sound passing through the air, such as sound produced by the subject during the exhalation. Advantageously, using these techniques, the subject may be tested at home using no more than a simple microphone, such as a microphone belonging to a smartphone or personal computer.

More specifically, in embodiments of the present invention, a processor computes one or more values of at least one parameter related to a concentration of a gas (e.g., $O_2$ or $CO_2$) in the exhaled air (which, in general, is the same as the concentration of the gas in the subject's lungs) at respective times during an exhalation of the subject, based on one or more properties of sound passing through the air at these times. The properties may include, for example, the speed of the sound (which may be measured directly) and/or spectral properties of the sound. Subsequently, the processor generates an output in response to the values.

For example, based on the values, the processor may compute a rate of change in the parameter and/or an equilibrium value of the parameter. Subsequently, based on the rate of change and/or the equilibrium value (e.g., based on comparing the rate of change and/or the equilibrium value to a suitable baseline), the processor may ascertain the subject's physiological state and then generate an output indicating the state. For example, in response to identifying an abnormality in the rate of change and/or the equilibrium value, the processor may generate an alert indicating that the subject's state with respect to a physiological condition may be unstable. Alternatively or additionally, the output may indicate the rate of change, the equilibrium value, and/or the values themselves, such that a physician may ascertain the subject's physiological state in response thereto.

In some embodiments, the processor computes the values of the parameter based on a speech signal representing speech of the subject. For example, the processor may select one or more portions of the speech signal, compute respective spectral envelopes of the portions, and compute the values of the parameter based on respective expansions or contractions of the spectral envelopes relative to respective corresponding baseline spectral envelopes. As described in detail below, these embodiments capitalize on the relationship between the concentration of $CO_2$ in (and hence, the molecular mass of) the air exhaled while the speech is uttered, and the spectrum of the speech signal representing this speech. For example, per this relationship, a higher concentration of $CO_2$ causes the spectral envelope of the signal to be more contracted (i.e., less expanded), relative to a lower concentration of $CO_2$.

In some embodiments, the parameter includes an "expansion-factor parameter," whose values, referred to herein as "expansion factors," quantify the relative expansions or contractions of the spectral envelopes. The expansion factor for each spectral envelope may be computed from the ratios between the formant frequencies in the spectral envelope and the corresponding formant frequencies in the baseline envelope. Alternatively, the expansion factor may be computed directly from spectral coefficients representing the spectral envelope.

Alternatively or additionally, the parameter may include the concentration of the gas. Alternatively or additionally, the parameter may include the molecular mass of the exhaled air. The values of the concentration, and/or the values of the molecular mass, may be derived from the expansion factors.

In other embodiments, the processor computes the values of the parameter based on measured speeds of sound passing through the exhaled air. The sound—which does not necessarily include speech sound, and is not even necessarily within an audible range of frequencies—may be produced by the subject during the exhalation, or it may be produced by another source, such as a speaker or an ultrasound transducer. The speeds may be measured by any suitable sensor, such as the aforementioned ultrasound transducer.

System Description

Reference is initially made to FIG. 1, which is a schematic illustration of a system 20 for evaluating the physiological state of a subject 22, in accordance with some embodiments of the present invention.

System 20 comprises an audio-receiving device 32, which is used by subject 22. Device 32 comprises circuitry, typically comprising an audio sensor 38 (e.g., a microphone), which converts sound waves to analog electrical signals, an analog-to-digital (A/D) converter 42, a processor 36, and a network interface, such as a network interface controller (NIC) 34. Typically, device 32 further comprises a storage device (e.g., a solid-state drive), a screen (e.g., a touchscreen), and/or other user interface components, such as a keyboard or a speaker. In some embodiments, device 32 comprises a mobile phone, a tablet computer, a laptop computer, a desktop computer, a voice-controlled personal assistant (such as an Amazon Echo™ or a Google Home™ device), a smart speaker device, or a dedicated medical device.

In some embodiments, audio sensor 38 (and, optionally, A/D converter 42) belong to a unit that is external to device 32. For example, audio sensor 38 may belong to a headset that is connected to device 32 by a wired or wireless connection, such as a Bluetooth connection.

In some embodiments, system 20 further comprises a temperature sensor configured to measure the temperature of the exhaled air of subject 22. The measured temperatures are received by processor 36, and are used by the processor to calculate the values of a relevant parameter related to a concentration of a gas in air in lungs of the subject, as further described below with reference to the subsequent figures.

For example, for embodiments in which audio sensor 38 belongs to a microphone in a headset, the temperature sensor may be mounted onto the microphone. The output signal of the temperature sensor may be encoded as an acoustic signal, e.g., by frequency modulation, such that A/D converter 42 receives a bi-channel stereo audio signal including both the output from the microphone and the acoustic signal from the temperature sensor.

Typically, system 20 further comprises a server 40, comprising circuitry comprising a processor 28, a storage device 30, such as a hard drive or flash drive, and a network interface, such as a network interface controller (NIC) 26.

Server 40 may further comprise a screen, a keyboard, and/or any other user interface components. Typically, server 40 is located remotely from device 32, e.g., in a control center, and server 40 and device 32 communicate with one another, via their respective network interfaces, over a network 24, which may include a cellular network and/or the Internet.

System 20 is configured to facilitate evaluating the subject's physiological state with respect to heart failure, asthma, hypobaropathy, hypercapnia (e.g., due to changes in altitude or air quality), Chronic Obstructive Pulmonary Disease (COPD), Interstitial Lung Disease (ILD), or any other physiological condition that affects the concentration of gases in the subject's lungs.

Typically, the system performs this function by processing one or more speech signals (also referred to herein as "speech samples") representing speech uttered by the subject during an exhalation. As further described below with reference to the subsequent figures, the system, based on the speech signals, computes one or more values of at least one parameter associated with the air in the lungs of the subject at respective times during the exhalation. The parameter may include, for example, the molecular mass of the air or the concentration of a gas, such as $CO_2$ or $O_2$, in the air.

In other embodiments, the system is configured to compute the values of the parameter based on measured speeds of sound in the exhaled air at the respective times during the exhalation. The speeds may be measured by any suitable sensor.

In some such embodiments, the sound is produced by the subject during the exhalation. Although the sound need not necessarily include speech, an advantage of speech is that, by virtue of the speech imposing a pattern of short inhalations and long exhalations, equilibrium concentrations are generally reached during the exhalations.

In other such embodiments, the sound is produced by another source. For example, the system may comprise an ultrasonic transducer 33 configured to emit sound (in the form of ultrasonic waves) into the exhaled air and to measure the speed of the sound, e.g., as described in Huang, Y. S., et al., "An accurate air temperature measurement system based on an envelope pulsed ultrasonic time-of-flight technique," Review of Scientific Instruments 78.11 (2007): 115102 or in Jedrusyna, A., "An Ultrasonic Air Temperature Meter," Recent Advances in Mechatronics, Springer, Berlin, Heidelberg, 2010, 85-89, the respective disclosures of which are incorporated herein by reference. While the speed of the sound is measured, the subject need not speak or produce any sound at all; nonetheless, speech may be advantageous by virtue of imposing a pattern of short inhalations and long exhalations, as described above.

The measured speeds of sound may be communicated, via any suitable communication interface, to processor 36 and/or processor 28. In response to the speeds, the processor may compute values of the molecular mass per equation (7). (For embodiments in which a temperature sensor is not used, an approximation for the temperature of the exhaled air, such as 307.5 K, may be used.) Subsequently, the processor may derive values of a gas concentration from the values of the molecular mass, e.g., per equation (2).

In yet other embodiments, the system, during a registration procedure, measures one or more properties of air exhaled by the subject or another subject. For example, the system may measure the speed of sound in the air, e.g., using the ultrasonic techniques described above. Alternatively or additionally, a baseline concentration of a gas (e.g., $CO_2$) in the air may be measured directly using any suitable sensor, e.g., as described in J. B. West et al., "Measurements of pulmonary gas exchange efficiency using expired gas and oximetry: results in normal subjects," Am. J. Physiol. Cell. Mol. Physiol., vol. 314, no. 4, pp. L686-L689, April 2018, whose disclosure is incorporated herein by reference. During this registration procedure, the subject need not speak or produce any sound at all; nonetheless, speech may be advantageous by virtue of imposing a pattern of short inhalations and long exhalations, as described above.

Subsequently to the registration, based on the measured properties, the processor computes parameter values (e.g., gas concentrations) with respect to the subject's test speech signals, as described below with reference to the subsequent figures. For example, for embodiments in which the speed of sound is measured during the registration, the processor may compute baseline values of the parameter based on the measured speeds of sound, and then compute the parameter values based on the baseline values.

In response to the values of the parameter, the system generates an output via any suitable output device, such as a display or a speaker. For example, based on the values of the parameter, the processor may estimate the state of the subject with respect to a physiological condition. Subsequently, the processor may include the estimated state, optionally with a likelihood associated with the estimation, in the output. Thus, for example, the output may indicate a likelihood that the subject is in a stable state, and/or a likelihood that the subject is in an unstable state, with respect to the condition. Alternatively or additionally, the output may include a score indicating the degree to which the subject's state appears to be unstable.

Typically, processor 36 of device 32 and processor 28 of server 40 cooperatively perform the receiving and processing of the speech samples. For example, as the subject speaks into device 32, the sound waves of the subject's speech may be converted to an analog signal by audio sensor 38, which may in turn be sampled and digitized by A/D converter 42. (In general, the subject's speech may be sampled at any suitable rate, such as a rate of between 8 and 45 kHz.) The resulting digital speech signal may be received by processor 36. Subsequently, processor 36 may communicate the speech signal, via NIC 34, to server 40, such that processor 28 receives the speech signal via NIC 26 and then processes the speech signal. Alternatively, processor 36 may process the speech signal, in which case the system need not necessarily comprise server 40. (Notwithstanding the above, the remainder of the present description, for simplicity, generally assumes that processor 28—also referred to hereinbelow simply as "the processor"—performs the processing.)

Subsequently to generating the aforementioned output, system 20 may communicate the output to the subject, to another person (e.g., the subject's physician), and/or to an electronic patient management system, which may integrate the output with other subject-specific information and take appropriate action.

For example, processor 28 may communicate the output to processor 36, and processor 36 may then communicate the output to the subject, e.g., by displaying a visual message on the display of device 32 and/or by playing an audio message using a speaker of device 32. Alternatively or additionally, in response to the output indicating a relatively high likelihood that the subject's state is unstable, the processor may communicate an alert indicating that the subject should take medication or visit a physician. The alert may be communicated by placing a call or sending a message (e.g., a text message) to the subject, to the subject's physician, and/or to a monitoring center. Alternatively or additionally, in response to the output, the processor may control a medication-administering device so as to adjust an amount of medication administered to the subject.

In some embodiments, device 32 comprises an analog telephone that does not comprise an A/D converter or a processor. In such embodiments, device 32 sends the analog audio signal from audio sensor 38 to server 40 over a telephone network. Typically, in the telephone network, the audio signal is digitized, communicated digitally, and then converted back to analog before reaching server 40. Accordingly, server 40 may comprise an A/D converter, which converts the incoming analog audio signal—received via a suitable telephone-network interface—to a digital speech signal. Processor 28 receives the digital speech signal from the A/D converter, and then processes the signal as described above. Alternatively, server 40 may receive the signal from the telephone network before the signal is converted back to analog, such that the server need not necessarily comprise an A/D converter.

As further described below with reference to the subsequent figures, processor 28, in processing the speech samples, may compare the spectral envelopes of the samples to baseline spectral envelopes. The baseline spectral envelopes, and/or reference speech signals to which the baseline spectral envelopes belong, may be received by processor 28 via NIC 26 and/or any other suitable communication interface, such as a flash-drive interface.

Processor 28 may be embodied as a single processor, or as a cooperatively networked or clustered set of processors. For example, a control center may include a plurality of interconnected servers comprising respective processors, which cooperatively perform the techniques described herein. In some embodiments, processor 28 belongs to a virtual machine.

In some embodiments, the functionality of processor 28 and/or of processor 36, as described herein, is implemented solely in hardware, e.g., using one or more Application-Specific Integrated Circuits (ASICs) or Field-Programmable Gate Arrays (FPGAs). Alternatively or additionally, the functionality of processor 28 and/or of processor 36 is implemented at least partly in software. For example, in some embodiments, processor 28 and/or processor 36 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Processing Speech Signals

Figure 2:
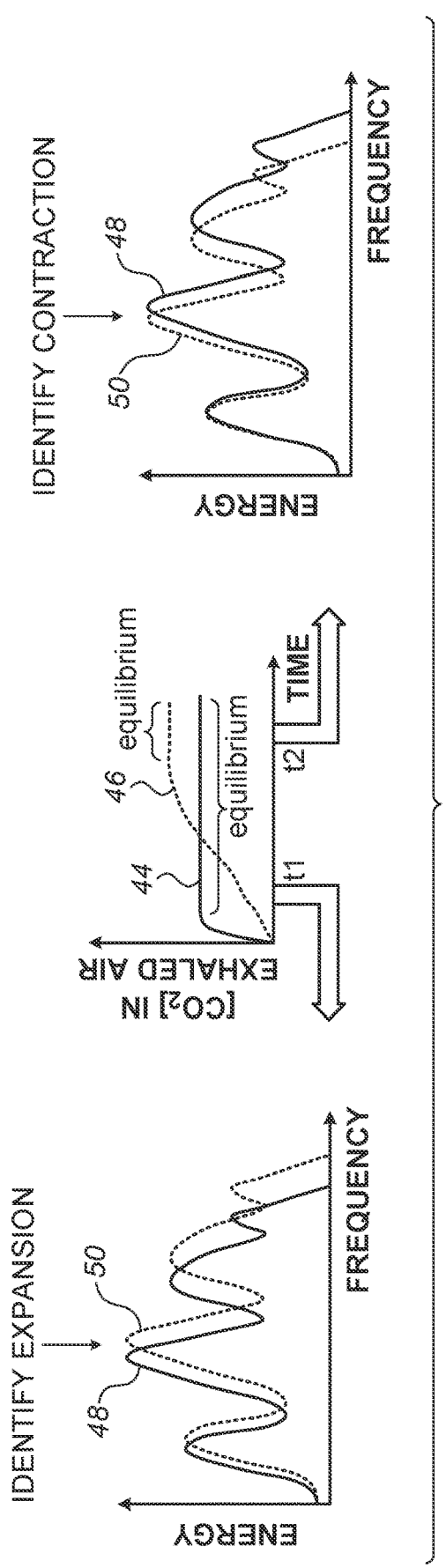
FIG. 2 illustrates an effect of $CO_2$ concentration in exhaled air on spectral properties of speech, which may be identified in accordance with some embodiments of the present invention.

Reference is now made to FIG. 2, which illustrates an effect of $CO_2$ concentration in exhaled air on spectral properties of speech, which may be identified in accordance with some embodiments of the present invention.

The center of FIG. 2 shows a first plot 44 of $CO_2$ concentration ($[CO_2]$) in exhaled air as a function of time during an exhalation performed, during speech, by a subject in a stable physiological state. Further shown is an analogous second plot 46 for the subject in an unstable state with respect to congestive heart failure or another condition that similarly affects the $CO_2$ concentration. As can be seen from the plots, the $CO_2$ concentration may increase at a slower rate in the unstable state, e.g., due to slower blood flow through the lungs and/or accumulation of fluid in the lungs, which impedes the diffusion of $CO_2$. Alternatively or additionally, the equilibrium $CO_2$ concentration may be higher in the unstable state, e.g., due to a higher concentration of $CO_2$ in the blood. Alternatively, for a subject suffering from hypocapnia (e.g., due to stroke, hyperthyroidism, hyperventilation, fear, stress, acute asthma, or COPD), the equilibrium $CO_2$ concentration may be lower than for the same subject in the stable state.

$CO_2$ has a significantly higher molecular mass than that of the other main gaseous components of exhaled air. Hence, in general, exhaled air having a higher concentration of $CO_2$ has a higher molecular mass than exhaled air having a lower concentration, such that, per equation (7), the speed of sound in the former is less than the speed of sound in the latter. (Although the exhaled air of the subject is generally not an ideal gas, embodiments of the present invention generally assume equation (7) to hold. Other, more complex formulae for non-ideal gases that may be used are described, for example, in O. Cramer, "The variation of the specific heat ratio and the speed of sound in air with temperature, pressure, humidity, and $CO_2$ concentration," J. Acoust. Soc. Am., vol. 93, no. 5, pp. 2510-2516, May 1993, whose disclosure is incorporated herein by reference.) The relationship between the speed of sound and the frequency "f" of the sound for a given wavelength "X" is given by the formula f=vλ. Thus, for any given subject, speech uttered with a greater speed of sound will generally have higher frequency content, relative to speech containing the same verbal content but uttered with a lesser speed of sound.

It follows, therefore, that the spectral properties of speech are affected by the level of $CO_2$ concentration in the air exhaled during the speech. This effect is illustrated in the left and right portions of FIG. 2. In particular, the left portion of FIG. 2 shows the spectral envelope 48 of the subject's speech in the stable state at a first time t1, assuming the spectral envelope is calculated for some arbitrary time window around time t1. Further shown is the spectral envelope 50 for the subject in the unstable state at the same time, assuming that the same verbal content is uttered in both states such that the shape of envelope 50 is generally the same as that of envelope 48. As can be seen, envelope 50 is expanded relative to envelope 48, due to the lower $CO_2$ concentration at t1 in the unstable state. Conversely, the right portion of FIG. 2, which shows envelope 48 and envelope 50 for a second time t2, shows the latter envelope contracted relative to the former, due to the higher $CO_2$ concentration at t2 in the unstable state.

More formally, letting w denote frequency, letting $H_0(\omega)$ denote spectral envelope 48, and letting $H_1(\omega)$ denote spectral envelope 50, it follows from the above that $H_1(\omega)=H_0(\omega/\beta)$, where $\beta=v_1/v_0$, i.e., the ratio of the speed of sound in the unstable-state exhalation to the speed of sound in the stable-state exhalation. Per equation (7), this ratio is equivalent to $$\sqrt{\frac{M_0 * T_1}{M_1 * T_0}},$$

where $M_0$ and $M_1$ are the respective molecular masses of the air exhaled in the stable and unstable states, and $T_0$ and $T_1$ are the respective temperatures of the exhaled air. Hence:

$$\beta = \sqrt{\frac{M_0 * T_1}{M_1 * T_0}}$$

$\beta$ is referred to below as the "expansion factor" of $H_1(\omega)$ relative to $H_0(\omega)$; $\beta>1$ indicates expansion, as at the left of FIG. 2, while $\beta<1$ indicates contraction, as at the right of FIG. 2.

As described in detail below with reference to the subsequent figures, the processor is configured to identify the degree to which the spectral envelopes of one or more portions of the speech signal received from subject 22 (FIG. 1), referred to below as the "test signal," are expanded or contracted. In particular, the processor may compute one or more expansion factors, each of which quantifies the expansion or contraction of the spectral envelope of a portion of the test signal relative to a corresponding baseline spectral envelope, such as spectral envelope 48.

Figure 3:
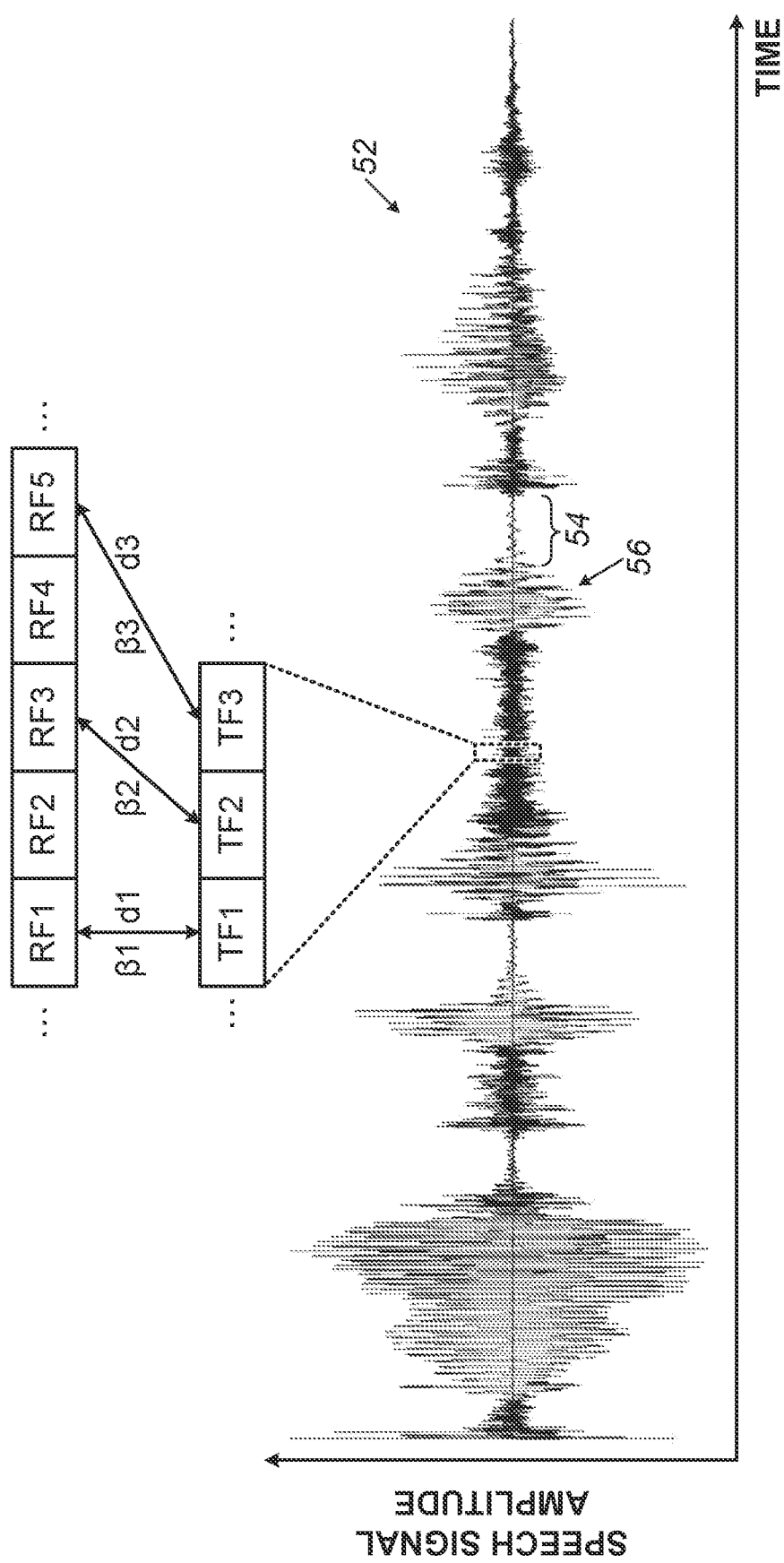
FIG. 3 is a schematic illustration of a technique for processing a test signal, in accordance with some embodiments of the present invention.

Reference is now made to FIG. 3, which is a schematic illustration of a technique for processing a test signal 52, which represents speech uttered by the subject, in accordance with some embodiments of the present invention.

Typically, the processor begins to process test signal 52 by identifying any breathing pauses 54 in signal 52, e.g., using voice activity detection (VAD). Subsequently, the processor divides the signal into segments 56, which are separated from each other by breathing pauses 54. The processor then selects one of segments 56 for further processing. Typically, subsequently to selecting the segment, the processor divides the segment into smaller portions referred to herein as "frames," the length of each frame typically being between 10 and 50 ms. By way of example, FIG. 3 shows three such frames TF1, TF2, and TF3.

Subsequently, the processor computes respective values of a parameter, such as the expansion-factor parameter or the molecular mass of the exhaled air, for the selected one or more portions (e.g., frames) of the test signal, by comparing the spectral envelopes of the portions to corresponding baseline spectral envelopes. Typically, the baseline spectral envelopes belong to respective baseline signal-portions corresponding to the selected portions of the test signal, respectively.

In some cases, the baseline signal-portions belong to a reference speech signal, i.e., a reference signal representing other speech uttered by the subject or by a different subject. (The reference signal may be stored, for example, in storage device 30 (FIG. 1).) This reference utterance may include any suitable verbal content, such as a designated sentence. Typically, the test utterance of the subject includes the same verbal content. (In some embodiments, the verbal content is chosen to be sufficiently long, and the subject is instructed not to inhale while uttering the utterance, such that equilibrium is reached during each utterance.)

In some such cases, the reference utterance is uttered by a speaker in a known physiological state, e.g., a stable state with respect to a physiological condition. Thus, the output generated by the processor (as described above with reference to FIG. 1) may indicate the physiological state of the subject relative to the known physiological state. For example, in response to values of P, which indicate the expansion or contraction of the test utterance relative to the reference utterance, the processor may generate an output indicating whether the subject's state is more or less stable than the known physiological state.

In other cases, the baseline signal-portions belong to the test signal. For example, when recording the test signal, the subject may repeat a word, or a short series of words, several times. Any portion of the test signal, such as a portion assumed to be at equilibrium, may then be designated as the baseline.

In some embodiments, the processor computes the values by executing a two-stage technique. First, the processor identifies a correspondence between the portions of the test signal and the baseline signal-portions. Next, the processor computes the expansion factors and, optionally, the values of another parameter responsively to the correspondence. In other embodiments, the processor executes a one-stage technique, per which the processor computes the values while finding the correspondence. Each of these techniques is described below.

By way of example, FIG. 3 shows five frames RF1, RF2, RF3, RF4, and RF5 belonging to a reference signal. As shown in FIG. 3, the processor may, using the one-stage or two-stage technique, find a correspondence between {TF1, TF2, TF3} and {RF1, RF3, RF5}. (This correspondence indicates that the verbal content of TF1 is similar to that of RF1, the verbal content of TF2 is similar to that of RF2, and the verbal content of TF3 is similar to that of RF3.)

The Two-Stage Technique

Per the two-stage technique, the processor first identifies the correspondence, using any suitable algorithm such as the Dynamic Time Warping (DTW) algorithm described in Sakoe and Chiba, "Dynamic Programming Algorithm Optimization for Spoken Word Recognition," IEEE Transactions on Acoustics, Speech, and Signal Processing 26.2 (1978): 43-49, whose disclosure is incorporated herein by reference.

Typically, the correspondence-finding algorithm minimizes a sum of respective distance measures between corresponding pairs of frames, subject to one or more suitable constraints. The distance measure between two frames may be defined, for example, as the distance (e.g., the Euclidean distance) between the spectral coefficients of the first frame and the spectral coefficients of the second frame. (The spectral coefficients, which represent the spectral envelope of the frame, may be computed using linear prediction, cepstral analysis, or any other suitable technique for short-time spectrum computation.) By way of example, FIG. 3 shows a distance d1 between TF1 and RF1, a distance d2 between TF2 and RF3, and a distance d3 between TF3 and RF5.

For example, the processor may first select a sequence of $N_t$ test-signal frames for which expansion factors are to be calculated. The processor may further calculate a sequence $\{v[n_t]\}$ for $n_t=1 \ldots N_t$, each $v[n_t]$ being a vector of spectral coefficients for the $n_t^{th}$ test-signal frame of the sequence. The processor may further identify $N_b$ baseline frames from which corresponding frames are to be found. The processor may also calculate a sequence $\{u[n_b]\}$ for $n_b=1 \ldots N_b$, each $u[n_b]$ being a vector of spectral coefficients for the $n_b^{th}$ baseline frame.

Subsequently, the processor may identify the correspondence between the test-signal frames and the baseline frames, by identifying the mapping $(n_t^1, n_b^1), (n_t^2, n_b^2), \ldots, (n_t^K, n_b^K)$ that pairs the $n_t^k$th test-signal frame with the $n_b^k$th baseline frame for $k=1 \ldots K$ such that the sum of distances between the pairs is minimized subject to one or more constraints. In other words, the processor may identify the mapping that minimizes $\Sigma_{k=1}^{K} w[k]*d(u[n_b^k], v[n_t^k])$, where $d(u[n_b^k], v[n_t^k])$ is the distance between $u[n_b^k]$ and $v[n_t^k]$ and $\{w[k]\}$ are respective weights for the pairs of frames. (Typically, at least some of the weights are different from each other.) Typically, $d(u[n_b^k], v[n_t^k]) = \|u[n_b^k] - v[n_t^k]\|_p$, p being greater than or equal to one, where $\|x\|_p$ indicates the LP norm of x. (The Euclidean distance is obtained for p=2.)

The constraints may include, for example, one or more of the following:
(i) The sequences $n_t^1 \ldots n_t^K$, and $n_b^1 \ldots n_b^K$ are non-decreasing.
(ii) The slopes $(n_t^{k+2}-n_t^k)/(n_b^{k+2}-n_b^k)$ k=1, ..., K−2, are within a predefined range, such as [0.5, 2] or [1/3, 3].
(iii) Each of the first and last pairs of indices is constrained to a predefined pair of integers, or to a small set of such pairs. For example, $(n_t^1, n_b^1)$ may be constrained to (1,1), and $(n_t^K, n_b^K)$ may be constrained to $(N_t, N_b)$.

Subsequently to identifying the correspondence, the processor calculates the expansion factors for the K test-signal frames relative to the K baseline frames, respectively. By way of example, FIG. 3 shows an expansion factor β1 for TF1 relative to RF1, an expansion factor β2 for TF2 relative to RF3, and an expansion factor β3 for TF3 relative to RF5.

It is noted that, in some cases, the same test-signal frame may correspond to multiple baseline frames, such that multiple expansion factors may be computed for the test-signal frame. In such a case, the processor may average the multiple expansion factors, or simply select one of the expansion factors.

Figure 4:
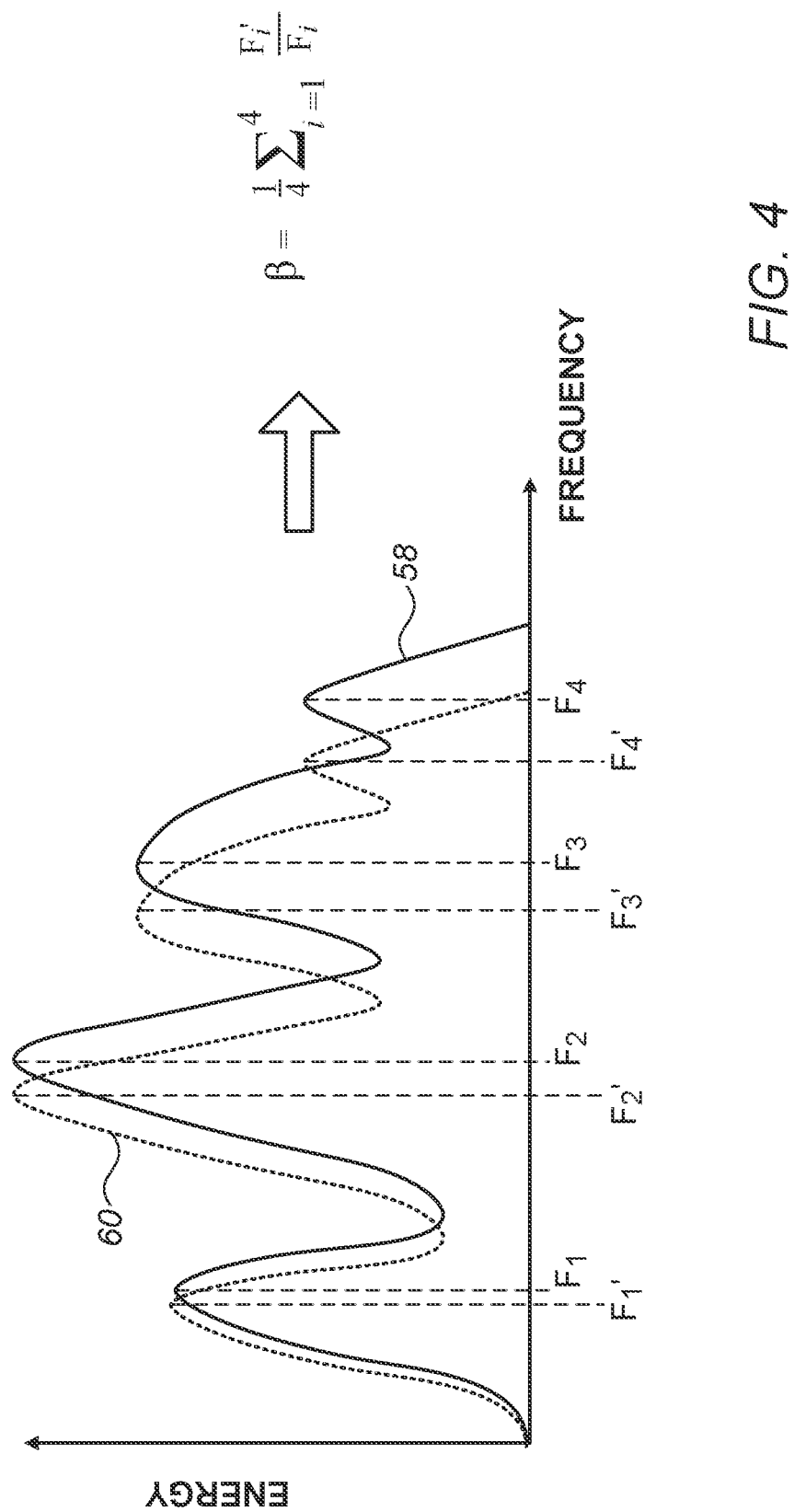
FIG. 4 is a schematic illustration of a technique for computing an expansion factor, in accordance with some embodiments of the present invention.

For further details regarding the computation of the expansion factors, reference is now made to FIG. 4, which is a schematic illustration of a technique for computing an expansion factor, in accordance with some embodiments of the present invention.

In some embodiments, the processor computes each expansion factor by computing a statistic (e.g., an average, such as a weighted average, or a median) of respective ratios between (i) one or more formant frequencies of the portion of the test signal for which the expansion factor is computed, and (ii) corresponding formant frequencies in the baseline spectrum for the portion.

By way of illustration, FIG. 4 shows a baseline spectral envelope 58 (belonging, for example, to a reference-signal frame such as RF1 of FIG. 3), along with the spectral envelope 60 of the corresponding test-signal frame (such as TF1 of FIG. 3). The formant frequencies of the baseline spectrum are $F_1$, $F_2$, $F_3$, and $F_4$. Spectral envelope 60 is contracted relative to baseline spectral envelope 58, such that the formant frequencies $F_1'$, $F_2'$, $F_3'$, and $F_4'$ of the spectrum of the test-signal frame are slightly smaller than $F_1$, $F_2$, $F_3$, and $F_4$, respectively. In other words, each formant frequency $F_i'$ of the spectrum of the test-signal frame is slightly smaller than the corresponding formant frequency $F_i$ of the baseline spectrum, for i=1 ... 4. In this scenario, the processor may compute the expansion factor by averaging $F_i'/F_i$ over i=1 ... 4. (In general, the processor may use any suitable technique known in the art to identify the formant frequencies of each spectrum.)

In other embodiments, rather than considering ratios between formant frequencies, the processor computes the expansion factor by utilizing a mathematical relationship between the expansion factor and the spectral coefficients that represent the spectral envelopes. As an example of such a relationship, expansion of a spectral envelope by a factor of 0 causes the $n^{th}$ cepstral coefficient $c_n'$ of the expanded envelope to have the value $$\sum_{k=-\infty}^{\infty} c_k \frac{\sin(\pi(k-n/\beta))}{\pi(k-n/\beta)},$$

where $c_k$ is the $k^{th}$ cepstral coefficient of the original envelope. (In practice, the above summation may be performed over values of k between n−j and n+j, j being an integer such as five, for example, without significant loss of precision.) In other words, applying the expansion factor β to the cepstral coefficient $c_n$ yields a new cepstral coefficient $$c_n' = \sum_{k=-\infty}^{\infty} c_k \frac{\sin(\pi(k-n/\beta))}{\pi(k-n/\beta)}.$$

Similar relationships exist for other types of spectral coefficients, such as Discrete Fourier Transform (DFT) coefficients.

In particular, in such embodiments, the processor computes the expansion factors such that the expansion factor for each of the test-signal portions minimizes a distance between (i) spectral coefficients v of the test-signal portion and (ii) baseline spectral coefficients u of the baseline spectrum for the test-signal portion, following an application of the expansion factor to u or v. In other words, the processor calculates each expansion factor such that the expansion factor minimizes the distance d(u', v), u' being the vector u following the application of β thereto, or the distance d(u, v'), v' being the vector v following the application of 1/β thereto. The distance d(x, y) between the two vectors of spectral coefficients may be calculated, for example, as $\|x-y\|_p$, p being greater than or equal to one.

In some embodiments, the processor minimizes the distance using an iterative optimization technique, such as the Newton-Raphson method. In other embodiments, the processor performs an exhaustive search for the optimal expansion factor over a discrete set of values within an expected range. For example, the processor may compute d(u', v) (or d(u, v')) for $\beta = 1 \pm j\delta$, j=0, . . . , J, where δ is a small step size, and then select the β yielding the minimum distance. In yet other embodiments, the processor executes the above two techniques in combination: first an exhaustive search is performed, and then the selected β is used as a starting point for an iterative optimization technique.

In some embodiments, the processor outputs the values of β without explicitly deriving values of any other parameter from the values of β.

In other embodiments, the processor derives one or more values of another parameter from the values of β, based on equation (8). Examples are hereby provided.

(a) An Equilibrium Molecular Mass or Gas Concentration

Provided the frames represent speech uttered after equilibrium was reached, the processor may compute an equilibrium molecular mass or concentration of a gas from the expansion factors. The processor may assume that equilibrium is reached after a threshold time from the start of the segment, the threshold time being between one and four seconds, for example.

For example, the processor may first compute a single equilibrium value SE from the individual values of β, e.g., by averaging the individual values. Subsequently, based on $\beta_E$, the processor may compute $M_{test,E}$, the equilibrium molecular mass of the air exhaled by the subject while uttering the test signal, and/or $C_{CO_2,test,E}$, the equilibrium concentration of $CO_2$ in the air (and in the lungs of the subject).

In particular, for embodiments in which a temperature sensor is used as described above with reference to FIG. 1, $M_{test,\ E}$ may be computed as $(M_{ref,\ E} * T_{test,E})/(\beta_E^2 * T_{ref,E})$, where $M_{ref,E}$ is the equilibrium molecular mass of the air exhaled by the subject while uttering the reference signal (or the baseline portion of the test signal), and $T_{test,E}$ and $T_{ref,E}$ are the temperatures of the air exhaled while uttering the equilibrium portions of the test and reference signals, respectively. For embodiments in which a temperature sensor is not used, it may be assumed that $T_{test,E}=T_{ref,E}$, such that $M_{test,E}=M_{ref,E}/\beta_E^2$.

$M_{ref,E}$ may be computed, for example, from the speed of sound measured (e.g., using the ultrasonic techniques described above with reference to FIG. 1) while the reference signal was uttered, per equation (7). (For embodiments in which the temperature T is not measured, an approximation for T, such as 307.5 K, may be used.) Alternatively, $M_{ref,E}$ may have any suitable estimated value, such as a value between 25 and 29 g/mol.

For $C_{CO_2,test,E}$, the processor may first compute $M_{test,E}$ as described above, and then compute $C_{CO_2,test,E}$, per equation (2), as $C_{CO_2,test,I}+(M_{test,E}-M_I)/12$, where $C_{CO_2,test,I}$ is the concentration of $CO_2$ at the start of the exhalation. Typically, $C_{CO_2,test,I} \approx 0$, such that $C_{CO_2,test,E} \approx (M_{test,E}-M_I)/12$.

Alternatively, for embodiments in which a baseline concentration of $CO_2$ is measured during the utterance of the reference signal as described above with reference to FIG. 1, the processor may compute $C_{CO_2,test,E}$ based on $C_{CO_2,ref,E}$, the equilibrium $CO_2$ concentration during the utterance of the reference signal. In particular, the processor may use the formula $C_{CO_2,test,E}=M_I*(\beta_E^{-2}-1)/12+(C_{CO_2,ref,E}-C_{CO_2,ref,I})/\beta_E^2 \approx M_I*(\beta_E^{-2}-1)/12+C_{CO_2,ref,E}/\beta_E^2$, which derives from substituting equation (2) for both $M_{test,E}$ and $M_{ref,E}$ into the equation $M_{test,E}=M_{ref,E}/\beta_E^2$.

(b) A Rate of Change in a Gas Concentration

Alternatively or additionally to computing an equilibrium value, the processor may compute a rate of change in the concentration of a gas, such as $CO_2$ or $O_2$, in the expired air. In particular, the processor may first compute multiple values of the concentration at different respective times. Subsequently, the processor may compute the rate of change based on the multiple values.

For example, the processor may first compute multiple values of the molecular mass, $\{M_{test}^k\}$, for at least some of the K test-signal frames for which the correspondence to the baseline was found. In particular, each $M_{test}^k$ may be computed as $(M_{ref}^k * M_{test}^k)/((\beta^k)^2 * T_{ref}^k)$ or, for embodiments in which a temperature sensor is not used, as $M_{ref}^k/(\beta^k)^2$, where $\beta^k$ is the expansion factor for the $k^{th}$ pair of frames. ($M_{ref}^k$ may be computed as described above for $M_{ref,E}$.)

Subsequently, based on $\{M_{test}^k\}$, the processor may identify the extent to which the rate of change in the concentration is perfusion-constrained. Subsequently, the processor may compute the rate of change in the concentration in response to identifying the extent to which the rate of change is perfusion-constrained. For example, the processor may compute $M'_{test}$, the discrete-time derivative of $\{M_{test}^k\}$. Next, the processor may compute the rate of change in the concentration based on $M'_{test}$ and at least one constant that depends on the extent to which the rate of change is perfusion-constrained.

For example, the processor may compute the rate of change as $C*M'_{test}$, where C is a constant depending on the extent to which the rate of change is perfusion-constrained. In this regard, reference is now made to FIG. 5, which schematically illustrates a technique for selecting the constant C, in accordance with some embodiments of the present invention. (The technique illustrated in FIG. 5 may be extended to selecting multiple constants for computing the rate of change in the concentration.)

Figure 5:
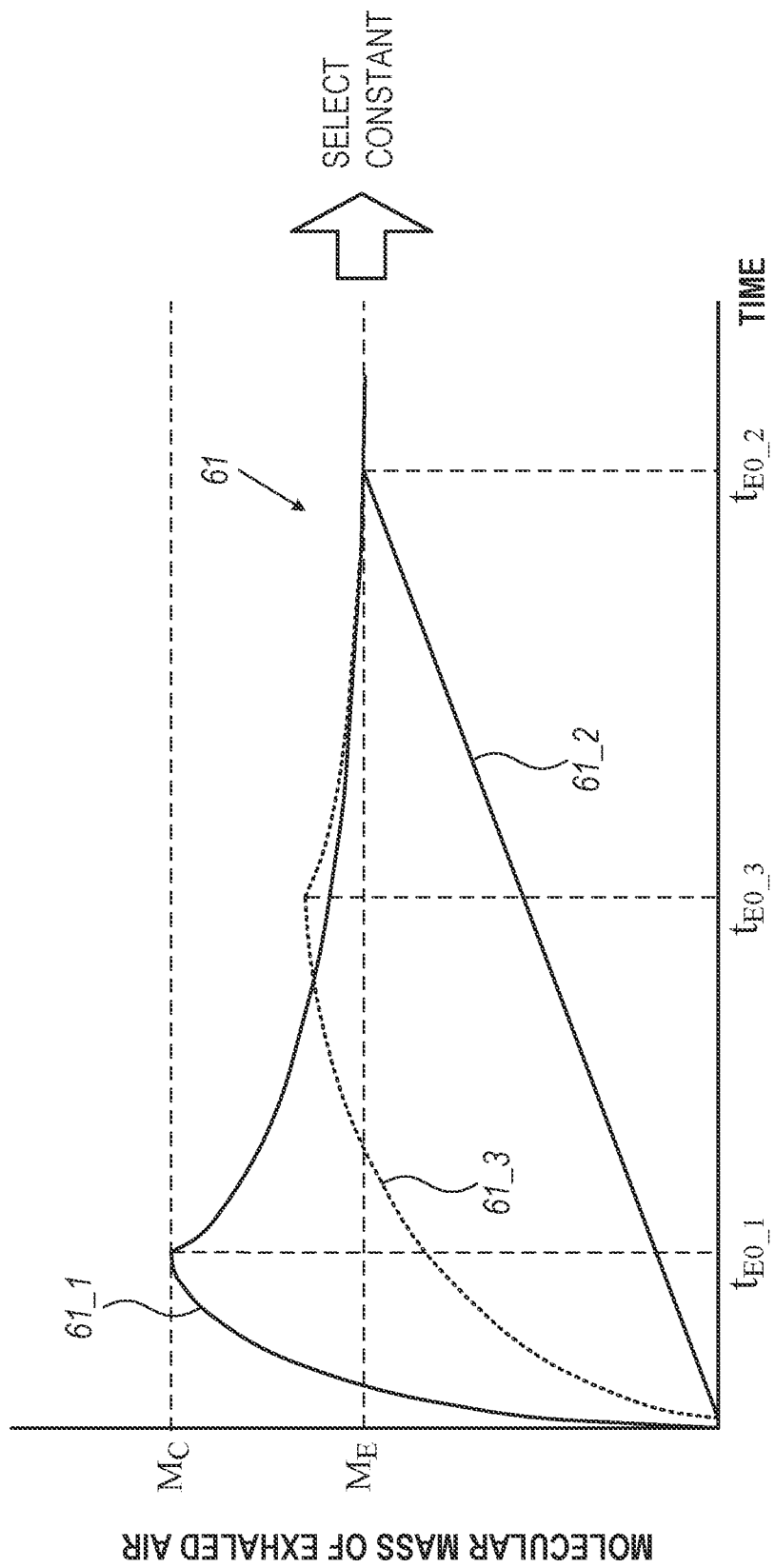
FIG. 5 schematically illustrates a technique for selecting a constant, in accordance with some embodiments of the present invention.

In some embodiments, respective predefined values of C are assigned to multiple functions 61, which represent the change over time in the molecular mass of exhaled air, or in the expansion factor, in various cases. For example, FIG. 5 shows three functions 61: a first function 61_1, corresponding to diffusion-constrained gas exchange, a second function 61_2, corresponding to perfusion-constrained gas exchange, and a third function 61_3, corresponding to partially-perfusion-constrained gas exchange. (The $CO_2$ concentration reaches equilibrium at a time $t_{E0\_1}$ for first function 61_1, a time $t_{E0\_2}$ for second function 612, and a time $t_{E0\_3}$ for third function 61_3.) Alternatively, functions 61 may include multiple functions corresponding to different respective extents of partial perfusion constraint.

By comparing $\{M_{test}^k\}$ or $\{\beta^k\}$ to functions 61, the processor identifies the extent to which the gas exchange is perfusion constrained, and selects C responsively thereto. For example, the processor may regress $\{M_{test}^k\}$ or $\{\beta^k\}$ to sets of function parameters that define functions 61, respectively. (The sets of function parameters may be stored in storage device 30 (FIG. 1), for example.) The processor may further identify the function for which the minimal regression error is received, and then select the value of C assigned to the identified function. Alternatively, the processor may identify a linear combination of the functions for which the regression error is minimal, and compute the corresponding linear combination of predefined C values.

(As a purely illustrative example, the function $\beta(t)=\sqrt{\beta_E^2 + K_1 e^{-t/\tau_1} - K_2 e^{-t/\tau_2}}$ for the case of diffusion constraint may be defined by the set of parameters $\{K_1, K_2, \tau_1, \tau_2\}$.)
Thus, for example:
(i) For diffusion-constrained exchange prior to $t_{E0}$, C may equal $1/(M_{CO_2}-M_I)$ for the rate of change in the concentration of $CO_2$, per equation (4).
(ii) For diffusion-constrained exchange subsequent to $t_{E0}$, C may equal $1/(M_{O_2}-M_I)$ for the rate of change in the concentration of $O_2$, per equation (5).
(iii) For perfusion-constrained exchange, C may equal $\pm 1/12$, per equation (6).

Optionally, prior to computing $M'_{test}$, the processor may smooth $\{M_{test}^k\}$ or $\{\beta^k\}$ such that the regression error is reduced to zero.

In other embodiments (e.g., based on the regression described above), the processor outputs an indication of the extent to which the rate of change in the gas concentration is perfusion constrained, without necessarily computing the rate of change.

In some embodiments, values of the relevant parameter, such as the equilibrium $CO_2$ concentration, are calculated for multiple segments 56, as further described below with reference to FIG. 6. In such embodiments, the processor may generate an output in response to the maximum, minimum, median, average, or any other statistic of the multiple parameter values.

The One-Stage Technique

Per the one-stage technique, the processor uses a modified form of the aforementioned correspondence-finding algorithm (e.g., DTW), which computes the values of the parameter while identifying the correspondence between the baseline signal-portions and the portions of the speech signal. In particular, the modified algorithm varies the correspondence and expands or contracts the spectral envelopes or the baseline spectral envelopes (i.e., applies an expansion factor $\beta$ or $1/\beta$ to each of the spectral envelopes or baseline spectral envelopes) so as to minimize a sum (e.g., a weighted sum) of respective distance measures for the portions. The distance measure for each of the portions is the distance between the spectral coefficients of the portion and the spectral coefficients of the baseline signal-portion to which the portion corresponds, following the expansion or contraction.

Typically, the minimization is performed under the constraints described above for the two-stage technique. Moreover, one or more additional constraints are imposed. For example, for cases in which the test frames were produced at equilibrium, the processor may require that the same expansion factor is applied to each of the frames, such that the resulting molecular mass is constant.

For example, after calculating $v[1], \ldots, v[N_t]$ and $u[1], \ldots, u[N_b]$, the processor may identify the mapping $(n_t^1, n_b^1, \beta^1, r^1), (n_t^2, n_b^2, \beta^2, r^2), \ldots, (n_t^K, n_b^K, \beta^K, r^K)$ that minimizes $\Sigma_{k=1}^K w[k]*d(u[n_b^k], v[n_t^k], \beta^k)$ subject to the constraints described above for the two-stage technique along with the additional constraints described below, where r is a binary "direction" variable indicating whether the molecular mass is increasing or decreasing, and $d(u[n_b^k], v[n_t^k], \beta^k) = d(u[n_b^k]', v[n_t^k])$ or $d(u[n_b^k], v[n_t^k]')$, where the "'" appendage indicates modification of the vector by $\beta^k$ or $1/\beta^k$ (respectively) as described above. (Each $\beta^k$ may be selected from a discrete set of potential values.) The additional constraints may be as follows. (The description below assumes a convention in which r=0 corresponds to an increase in the molecular mass, while r=1 corresponds to a decrease. In some embodiments, the opposite convention is used.)
(a) $r^1=0$, and $r^k=1$ if $r^{k-1}=1$. (This constraint requires that the molecular mass increase initially and change direction only once.)
(b) Each $\beta^k$ is such that $\beta^k \leq \beta^{k+1} \leq \beta^k + \varepsilon_0$ for $r^k=1$ and $\beta^k - \varepsilon_1 \leq \beta^{k+1} \leq \beta^k$ for $r^k=0$, where $\varepsilon_0$ and $\varepsilon_1$ are suitable constants. (This constraint ensures smoothness and monotonicity.)

Alternatively or additionally to the latter constraint, for cases in which the test frames were produced prior to equilibrium, the processor may require that the resulting molecular mass or expansion factor vary in accordance with a predefined parametric function, such as any one of functions 61 or a linear combination thereof.

Subsequently, the processor may generate an output responsively to the parameter values that were computed while finding the correspondence. Alternatively or additionally, the processor may compute the values of another parameter; for example, the processor may compute gas concentrations from $\{\beta^k\}$ or $\{M_{test}^k\}$, as described above for the one-stage technique. Subsequently, the output may be generated responsively to these additional parameter values.

Example Algorithm

Figure 6:
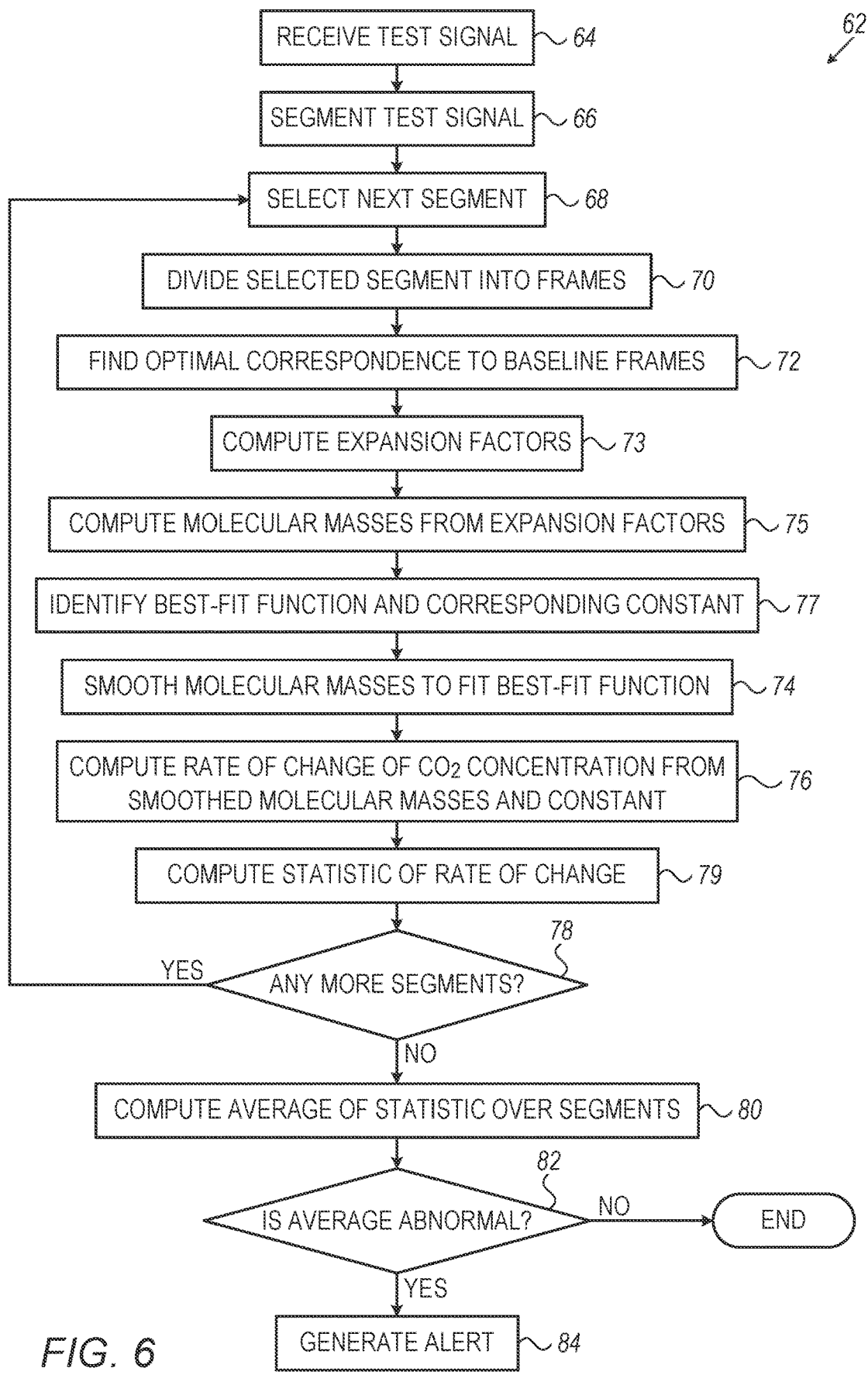
FIG. 6 is a flow chart for an example algorithm for processing a test speech signal, in accordance with some embodiments of the present invention.

Reference is now made to FIG. 6, which is a flow chart for an example algorithm 62 for processing a test speech signal, in accordance with some embodiments of the present invention.

Algorithm 62 begins with a signal-receiving step 64, at which the processor receives a test signal from the subject, e.g., over network 24 (FIG. 1). Subsequently to receiving the test signal, the processor, at a signal-segmenting step 66, segments the test signal by identifying any breathing pauses in the signal, as described above with reference to FIG. 3. Typically, the subject is instructed, when generating the test signal, to repeat the same utterance several times, pausing to inhale between the utterances; hence, the segments of the test signal typically represent the same verbal content.

Next, at a segment-selecting step 68, the processor selects one of the segments (or a portion thereof). Subsequently, at a dividing step 70, the processor divides the selected segment into frames. The processor then computes the rate of change of $CO_2$ concentration over the period of time spanned by the selected segment.

For example, using the two-stage technique, the processor may, at an optimizing step 72, find the optimal correspondence of the test-signal frames to baseline frames. (As described above with reference to FIG. 3, the baseline frames may be extracted from a reference signal or from the test signal itself.) Subsequently, at a computing step 73, the processor may compute respective expansion factors for the test-signal frames. Next, at another computing step 75, the processor may compute molecular masses (i.e., $\{M_{test}^k\}$) from the expansion factors. Subsequently, at an identifying step 77, the processor may identify the function that the molecular masses fit best (i.e., the function for which the regression error is smallest), along with the corresponding constant C. (As described above with reference to FIG. 5, this constant may be computed as a linear combination of predefined constants.) Next, at a smoothing step 74, the processor may smooth the molecular masses to fit the best-fit function. Finally, at another computing step 76, the processor may compute the rate of change of the $CO_2$ concentration based on the smoothed molecular masses and the identified constant C.

Subsequently, at another computing step 19, the processor computes a statistic, such as an average or maximum, of the rate of change over the frames.

Subsequently, the processor checks, at a checking step 78, whether any unselected segments remain. If yes, the processor returns to segment-selecting step 68.

Following the computation of the statistic for each segment, the processor, at an averaging step 80, computes the average of the statistic over the segments. In doing so, the processor may weight the segments differently, discard outliers, and/or use any other techniques known in the art for increasing the reliability of the average. (Alternatively to an average, the processor may compute a median or any other suitable statistic.)

Next, the processor, at a comparing step 82, compares the average to a suitable predefined threshold. If the average passes the threshold, the value of the parameter is deemed to be abnormal. (Depending on the parameter and on the physiological condition with respect to which the subject is being tested, an abnormal value may either be less than or greater than the threshold.) In response to identifying the abnormality, the processor generates an alert at an alert-generating step 84. Otherwise, algorithm 62 ends without the generation of an alert.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
    an output device; and
    one or more processors configured to cooperatively carry out a process that includes:
        receiving a speech signal representing speech uttered by a subject,
        processing the speech signal so as to identify one or more properties of the speech that depend on a concentration of a gas in air exhaled by the subject while uttering the speech,
        based on the properties, computing one or more values of at least one parameter at respective times during the speech, the parameter being related to the concentration of the gas, and
        generating an output, via the output device, in response to the values.

2. The system according to claim 1, further comprising a sensor configured to measure a speed of sound in the air, wherein the process includes computing the values based on the speed.

3. The system according to claim 1, further comprising a sensor configured to measure a baseline concentration of the gas in other exhaled air, wherein the process includes computing the values based on the baseline concentration of the gas.

4. A method, comprising:
    receiving a speech signal representing speech uttered by a subject;
    processing the speech signal so as to identify one or more properties of the speech that depend on a concentration of a gas in air exhaled by the subject while uttering the speech,
    based on the properties, computing one or more values of at least one parameter at respective times during the speech, the parameter being related to the concentration of the gas; and
    generating an output in response to the values.

5. The method according to claim 4, wherein the output indicates a state of the subject with respect to a physiological condition selected from the group of conditions consisting of: heart failure, asthma, hypobaropathy, hypercapnia, Chronic Obstructive Pulmonary Disease (COPD), and Interstitial Lung Disease (ILD).

6. The method according to claim 4, further comprising, based on the values, identifying an extent to which a rate of change in the concentration of the gas is perfusion-constrained, wherein the output indicates the extent to which the rate of change is perfusion-constrained.

7. The method according to claim 4,
    wherein computing the one or more values of the at least one parameter comprises computing multiple values of the concentration of the gas,
    wherein the method further comprises, based on the multiple values of the concentration of the gas, computing a rate of change of the concentration of the gas, and
    wherein generating the output comprises generating the output in response to the rate of change.

8. The method according to claim 7, wherein generating the output comprises generating the output in response to comparing the rate of change to a baseline rate of change.

9. The method according to claim 7,
wherein computing the one or more values of the at least one parameter further comprises computing multiple molecular-mass values of a molecular mass of the air,
wherein the method further comprises identifying an extent to which the rate of change is perfusion-constrained, and
wherein computing the rate of change comprises computing the rate of change based on the molecular-mass values and in response to identifying the extent to which the rate of change is perfusion-constrained.

10. The method according to claim 9, wherein computing the rate of change comprises computing the rate of change as a function of:
another rate of change of the molecular mass, and
at least one constant that depends on the extent to which the rate of change is perfusion-constrained.

11. The method according to claim 4, wherein the one or more values include an equilibrium value of the parameter.

12. The method according to claim 11, wherein the equilibrium value includes a $CO_2$-equilibrium value of a $CO_2$-concentration of $CO_2$ in the air.

13. The method according to claim 12, wherein computing the $CO_2$-equilibrium value comprises computing the $CO_2$-equilibrium value based on a baseline $CO_2$-equilibrium value that was measured prior to the speech.

14. The method according to claim 4, wherein computing the values comprises:
selecting portions of the speech signal recorded at the times, respectively;
computing respective spectral envelopes of the portions; and
computing the values based on respective expansions or contractions of the spectral envelopes relative to respective corresponding baseline spectral envelopes.

15. The method according to claim 14, wherein the values include respective expansion factors that quantify the expansions or contractions.

16. The method according to claim 14, wherein the baseline spectral envelopes belong to respective baseline signal-portions corresponding to the portions of the signal, respectively.

17. The method according to claim 16, wherein the baseline signal-portions are other portions of the speech signal.

18. The method according to claim 16, wherein the baseline signal-portions belong to a reference speech signal.

19. The method according to claim 18, wherein the reference speech signal represents other speech uttered while in a known physiological state, and wherein the output indicates a physiological state of the subject relative to the known physiological state.

20. The method according to claim 18, wherein the reference speech signal represents other speech, and wherein computing the values comprises computing the values based on one or more measured properties of other air exhaled during the other speech.

21. The method according to claim 18, wherein the reference speech signal represents other speech uttered by the subject.

22. The method according to claim 16, wherein computing the values comprises computing the values while identifying the correspondence between the baseline signal-portions and the portions of the speech signal, by varying the correspondence and expanding or contracting the spectral envelopes or the baseline spectral envelopes so as to minimize a sum of respective distance measures for the portions, the distance measure for each of the portions being a distance between (i) spectral coefficients of the portion and (ii) baseline spectral coefficients of the baseline signal-portion to which the portion corresponds, following the expansion or contraction.

23. The method according to claim 22, wherein computing the values comprises computing the values under a constraint that the values vary in accordance with a pre-defined function.

24. The method according to claim 16, further comprising, prior to computing the values, identifying the correspondence between the portions and the baseline signal-portions by minimizing a sum of respective distance measures for the portions, the distance measure for each of the portions being a distance between (i) spectral coefficients of the portion and (ii) baseline spectral coefficients of the baseline signal-portion to which the portion corresponds.

25. The method according to claim 24, wherein computing the values comprises computing the values based on, for each of the portions, a statistic of respective ratios between (i) one or more formant frequencies of the portion, and (ii) corresponding formant frequencies in the baseline spectrum for the portion.

26. The method according to claim 24, wherein the values include respective expansion factors that quantify the expansions or contractions, and wherein the expansion factor for each portion minimizes a distance between (i) spectral coefficients of the portion and (ii) baseline spectral coefficients of the baseline spectrum for the portion, following an application of the expansion factor to the spectral coefficients or to the baseline spectral coefficients.

27. The method according to claim 4, wherein computing the values comprises computing the values based on respective measured speeds of sound in the air.

28. A computer software product comprising a tangible non-transitory computer-readable medium in which program instructions are stored, which instructions, when read by one or more processors, cause the processors to cooperatively carry out a process that includes:
receiving a speech signal representing speech uttered by a subject,
processing the speech signal so as to identify one or more properties of the speech that depend on a concentration of a gas in air exhaled by the subject while uttering the speech,
based on the properties, computing one or more values of at least one parameter at respective times during the speech, the parameter being related to the concentration of the gas, and
generating an output in response to the values.

29. The computer software product according to claim 28, wherein the output indicates a state of the subject with respect to a physiological condition selected from the group of conditions consisting of: heart failure, asthma, hypobaropathy, hypercapnia, Chronic Obstructive Pulmonary Disease (COPD), and Interstitial Lung Disease (ILD).

30. The computer software product according to claim 28, wherein the process further includes, based on the values, identifying an extent to which a rate of change in the concentration of the gas is perfusion-constrained, and wherein the output indicates the extent to which the rate of change is perfusion-constrained.

31. The computer software product according to claim 28,
wherein computing the one or more values of the at least one parameter includes computing multiple values of the concentration of the gas,
wherein the process further includes, based on the multiple values of the concentration of the gas, computing a rate of change of the concentration of the gas, and
wherein generating the output includes generating the output in response to the rate of change.

32. The computer software product according to claim 31, wherein generating the output includes generating the output in response to comparing the rate of change to a baseline rate of change.

33. The computer software product according to claim 31,
wherein computing the one or more values of the at least one parameter further includes computing multiple molecular-mass values of a molecular mass of the air,
wherein the process further includes identifying an extent to which the rate of change is perfusion-constrained, and
wherein computing the rate of change includes computing the rate of change based on the molecular-mass values and in response to identifying the extent to which the rate of change is perfusion-constrained.

34. The computer software product according to claim 28, wherein the one or more values include an equilibrium value of the parameter.

35. The computer software product according to claim 34, wherein the equilibrium value includes a $CO_2$-equilibrium value of a $CO_2$-concentration of $CO_2$ in the air.

36. The computer software product according to claim 28, wherein computing the values includes:
selecting portions of the speech signal recorded at the times, respectively,
computing respective spectral envelopes of the portions, and
computing the values based on respective expansions or contractions of the spectral envelopes relative to respective corresponding baseline spectral envelopes.

37. The computer software product according to claim 36, wherein the values include respective expansion factors that quantify the expansions or contractions.

38. The computer software product according to claim 36, wherein the baseline spectral envelopes belong to respective baseline signal-portions corresponding to the portions of the signal, respectively.

39. The computer software product according to claim 38, wherein the baseline signal-portions are other portions of the speech signal.

40. The computer software product according to claim 38, wherein the baseline signal-portions belong to a reference speech signal.

41. The computer software product according to claim 38, wherein computing the values includes computing the values while identifying the correspondence between the baseline signal-portions and the portions of the speech signal, by varying the correspondence and expanding or contracting the spectral envelopes or the baseline spectral envelopes so as to minimize a sum of respective distance measures for the portions, the distance measure for each of the portions being a distance between (i) spectral coefficients of the portion and (ii) baseline spectral coefficients of the baseline signal-portion to which the portion corresponds, following the expansion or contraction.

42. The computer software product according to claim 41, wherein computing the values includes computing the values under a constraint that the values vary in accordance with a predefined function.

43. The computer software product according to claim 38, wherein the process further includes, prior to computing the values, identifying the correspondence between the portions and the baseline signal-portions by minimizing a sum of respective distance measures for the portions, the distance measure for each of the portions being a distance between (i) spectral coefficients of the portion and (ii) baseline spectral coefficients of the baseline signal-portion to which the portion corresponds.

44. The computer software product according to claim 28, wherein computing the values includes computing the values based on respective measured speeds of sound in the air.

* * * * *